(12) United States Patent
Atre et al.

(10) Patent No.: US 10,551,330 B2
(45) Date of Patent: Feb. 4, 2020

(54) NANOSCALE OPTICAL TOMOGRAPHY WITH CATHODOLUMINESCENCE SPECTROSCOPY

(71) Applicants: THE BOARD OF TRUSTEES OF THE LELAND STANFORD JUNIOR UNIVERSITY, Stanford, CA (US); STICHTING VOOR FUNDAMENTEEL ONDERZOEK DER MATERIE, Utrecht (NL); Ashwin C. Atre, Stanford, CA (US); Jennifer A. Dionne, Stanford, CA (US); Benjamin Brenny, Utrecht (NL); Toon Coenen, Utrecht (NL); Albert Polman, Utrecht (NL)

(72) Inventors: Ashwin C. Atre, Stanford, CA (US); Jennifer A. Dionne, Stanford, CA (US); Benjamin Brenny, Utrecht (NL); Toon Coenen, Utrecht (NL); Albert Polman, Utrecht (NL)

(73) Assignees: THE BOARD OF TRUSTEES OF THE LELAND STANFORD JUNIOR UNIVERSITY, Stanford, CA (US); STICHTING VOOR FUNDAMENTEEL ONDERZOEK DER MATERIE, Utrecht (NL)

( * ) Notice: Subject to any disclaimer, the term of this patent is extended or adjusted under 35 U.S.C. 154(b) by 111 days.

(21) Appl. No.: 15/305,329

(22) PCT Filed: Apr. 22, 2015

(86) PCT No.: PCT/US2015/027125
§ 371 (c)(1),
(2) Date: Oct. 19, 2016

(87) PCT Pub. No.: WO2016/007208
PCT Pub. Date: Jan. 14, 2016

(65) Prior Publication Data
US 2017/0052130 A1 Feb. 23, 2017

Related U.S. Application Data

(60) Provisional application No. 61/982,675, filed on Apr. 22, 2014.

(51) Int. Cl.
*G01N 23/2254* (2018.01)
*A61B 5/00* (2006.01)
*G01J 3/44* (2006.01)

(52) U.S. Cl.
CPC .......... *G01N 23/2254* (2013.01); *A61B 5/00* (2013.01); *A61B 5/0073* (2013.01); *G01J 3/44* (2013.01); *A61B 5/0075* (2013.01)

(58) Field of Classification Search
None
See application file for complete search history.

(56) References Cited

U.S. PATENT DOCUMENTS 9,468,409 B2 * 10/2016 Claus .................... A61B 6/025
9,541,512 B2 * 1/2017 Walsworth ......... G01N 23/2254
(Continued)

FOREIGN PATENT DOCUMENTS

WO  WO-2012/174173 A2  12/2012
WO  WO 201217417 A2 * 12/2012 ......... G01N 23/2254
(Continued)

OTHER PUBLICATIONS

Crowther, R.A. et al. (1970) "The reconstruction of a three-dimensional structure from projections and its application to electron microscopy," Proc. R. Soc. Lond. A 317:319-340.
(Continued)

*Primary Examiner* — Andrew Smyth
(74) *Attorney, Agent, or Firm* — Foley & Lardner LLP; Cliff Z. Liu

(57) ABSTRACT

In one aspect, a cathodoluminescence (CL) spectroscopic tomography device includes a sample stage to support a sample. An electron beam source scans an electron beam over the sample to yield light emission by the sample. A reflective element directs the light emission by the sample to a light detector. A controller controls operation of the sample stage, the electron beam source, and the light detector. In one aspect, a CL spectroscopic tomography device includes an electron beam source which directs an electron beam at an object to yield an emission by the object. A detector detects the emission. A controller receives information from the detector related to the detected emission. The controller derives a two-dimensional (2D) CL map from the informa-
(Continued)

tion related to the detected emission, and derives a three-dimensional (3D) CL tomogram from the 2D CL map.

9 Claims, 20 Drawing Sheets

(56) References Cited

U.S. PATENT DOCUMENTS

| | | | |
|---|---|---|---|
| 2010/0059672 A1* | 3/2010 | Zeile | G01N 23/2251 250/282 |
| 2013/0015351 A1* | 1/2013 | Kooijman | G01N 23/2206 250/307 |
| 2013/0068966 A1* | 3/2013 | Kociak | G01N 23/2254 250/458.1 |
| 2013/0140459 A1* | 6/2013 | Galloway | H01J 37/02 250/310 |
| 2013/0193342 A1* | 8/2013 | Berney | G01N 23/2254 250/399 |
| 2013/0264483 A1* | 10/2013 | Abenaim | G01T 1/2018 250/363.01 |
| 2014/0027632 A1* | 1/2014 | Stowe | G01N 23/2254 250/306 |
| 2014/0153690 A1* | 6/2014 | Claus | A61B 6/025 378/9 |

FOREIGN PATENT DOCUMENTS

| | | | | |
|---|---|---|---|---|
| WO | WO-2012174173 A2 * | 12/2012 | | G01N 23/2254 |
| WO | WO 201217417 A3 * | 3/2013 | | G01N 23/2254 |
| WO | WO-2012174173 A3 * | 3/2013 | | G01N 23/2254 |

OTHER PUBLICATIONS

De Winter, D. et al. (2011) "FIB-SEM cathodoluminescence tomography: practical and theoretical considerations," J. Microsc. 243(3):315-326.
García De Abajo, F.J. et al. (2008) "Probing the photonic local density of states with electron energy loss spectroscopy," Phys. Rev. Lett. 100:106804-1-106804-4.
Huang, B. et al. (2008) "Three-dimensional super-resolution imaging by stochastic optical reconstruction microscopy," Science 319(5864):810-813.
International Search Report and Written Opinion (ISR/WO) in International Application No. PCT/US2015/027125, dated Feb. 2, 2016.
Knight, M.W. et al. (2008) "Nanoshells to nanoeggs to nanocups: optical properties of reduced symmetry core-shell nanoparticles beyond the quasistatic limit," New J. Phys. 10:105006, 10 pages.
Lu, Y. et al. (2005) "Nanophotonic crescent moon structures with sharp edge for ultrasensitive biomolecular detection by local electromagnetic field enhancement effect," Nano Lett. 5(1):119-124.
Van Aert, S. et al. (2011) "Three-dimensional atomic imaging of crystalline nanoparticles," Nature 470:374-377.
Wang, X.Y. et al. (2012) "Reconstruction and visualization of nanoparticle composites by transmission electron tomography," Ultramicroscopy 113:96-105.
Arslan et al., "Reducing the missing wedge: High-resolution dual axis tomography of inorganic materials", Ultramicroscopy 106 (2006), pp. 994-1000.
Atre et al., "Nanoscale optical tomography with cathodoluminescence spectroscopy", Nature Nanotechnology, Articles, Apr. 6, 2015, 8 pages.
Atre et al., "Nanoscale optical tomography with cathodoluminescence spectroscopy", Nature Nanotechnology, Supplementary Information, 2015, 27 pages.
Lyra et al., "Filtering in SPECT Image Reconstruction", International Journal of Biomedical Imaging, vol. 2011, 14 pages.

* cited by examiner

NANOSCALE OPTICAL TOMOGRAPHY WITH CATHODOLUMINESCENCE SPECTROSCOPY

CROSS-REFERENCE TO RELATED PATENT APPLICATIONS

This application is a national phase entry under 35 U.S.C. § 371 of International Application No. PCT/US2015/027125, filed Apr. 22, 2015, which claims the benefit of and priority to U.S. Provisional Patent Application No. 61/982,675 filed Apr. 22, 2014 to Atre et al., titled "Nanoscale Optical Tomography with Cathodoluminescence Spectroscopy," the contents of each of which are incorporated herein by reference in their entirety.

STATEMENT REGARDING FEDERALLY SPONSORED RESEARCH OR DEVELOPMENT

This invention was made with Government support under contract FA9550-11-1-0024 awarded by the Air Force Office of Scientific Research, under contract DE-EE0005331 awarded by the Department of Energy, and under contract DMR-1151231 awarded by the National Science Foundation. The Government has certain rights in the invention.

BACKGROUND

Tomography allows the determination of a three-dimensional function from two-dimensional data. Originally driven to provide for non-invasive techniques to peer inside the human body, the development and application of tomography has had a significant impact on a wide range of disciplines, from medical diagnosis to oceanography and seismology. Conventional tomographic techniques yield three-dimensional structural or chemical information with macroscopic resolution, while recent advances in electron microscopy have allowed nanoscale reconstruction of material geometries.

Still, optical tomography with sub-wavelength, nanometer-scale resolution remains a significant challenge. Capturing the often complex three-dimensional nature of light-matter interactions with nanometer-scale spatial and spectral resolution remains a significant challenge.

SUMMARY

In one aspect, a cathodoluminescence (CL) spectroscopic tomography device includes a sample stage to support a sample. An electron beam source scans an electron beam over the sample to yield light emission by the sample. A reflective element directs the light emission by the sample to a light detector. A controller controls operation of the sample stage, the electron beam source, and the light detector.

In one aspect, a CL spectroscopic tomography device includes an electron beam source which directs an electron beam at an object to yield an emission by the object. A detector detects the emission. A controller receives information from the detector related to the detected emission. The controller derives a two-dimensional (2D) CL map from the information related to the detected emission, and derives a three-dimensional (3D) CL tomogram from the 2D CL map.

In one aspect, a method includes controlling a detector to measure intensity of emissions from an object resulting from an electron beam scanned across the object, receiving from the detector information related to the measured intensity, deriving from the received information a plurality of 2D CL maps, and deriving from the 2D CL maps a 3D CL tomogram.

DETAILED DESCRIPTION

Acronyms and Abbreviations nanometer (nm)
micrometer (μm)
millimeter (mm)
centimeter (cm)
kiloelectron-volt (keV)
two-dimensional (2D)
three-dimensional (3D)
revolutions per minute (rpm)
cathodoluminescence (CL)
CL analysis (CLA)
local density of optical states (LDOS)
electron-energy loss spectroscopy (EELS)
transmission electron microscopy/microscope (TEM)
scanning electron microscopy/microscope (SEM)
finite-difference time-domain (FDTD)
boundary element method (BEM)
Purcell factor (PF)
photoluminescence (PL)
application-specific integrated circuit (ASIC)
field programmable gate array (FPGA)
programmable logic device (PLD)

The present disclosure describes techniques for analysis of objects based on detection of CL. Among other benefits, the techniques allow for probing of radiative optical properties at nanoscale spatial resolution, nanoscale spectral resolution, and without fluorescent tags. A further benefit is that 3D images of the optical properties may be reconstructed.

Figure 1A:
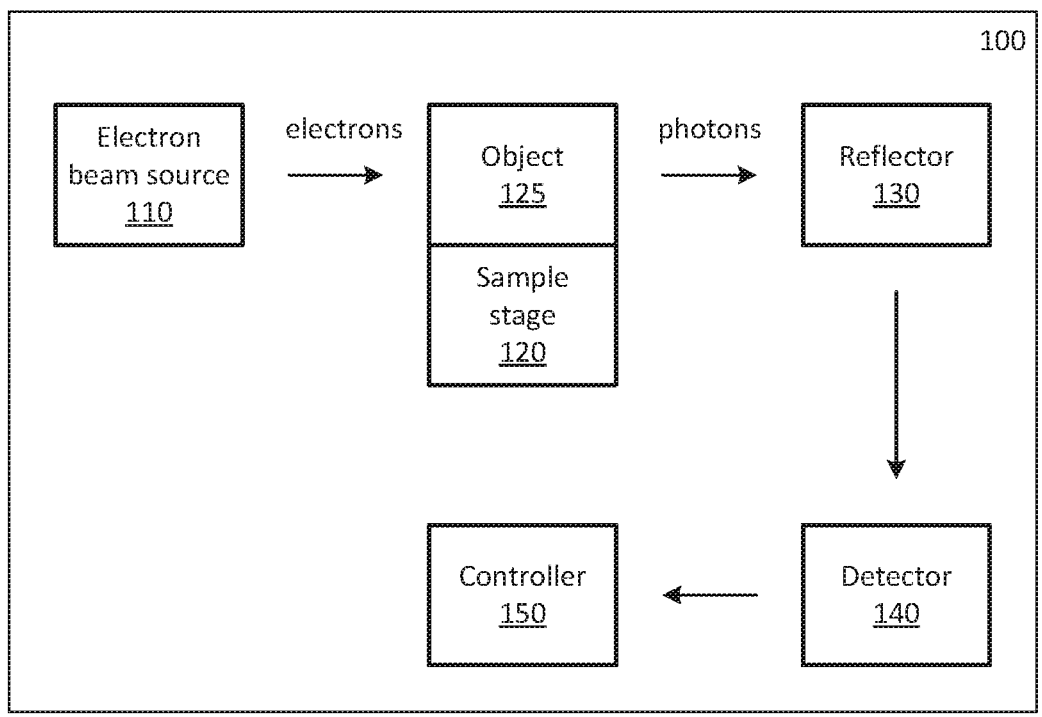
FIG. 1A represents an example of a system for object analysis.

FIG. 1A provides an example, by way of overview, of a system 100 for object analysis based on CL detection. System 100 includes an electron beam source 110, a sample stage 120, a reflector 130, a detector 140, and a controller 150. Electron beam source 110 directs an electron beam towards an object 125 positioned on (or at) sample stage 120. Upon impact of the electrons on object 125, photons with visible and near infrared wavelengths (e.g., light) are released from object 125 according to the CL properties of object 125. The light is reflected by reflector 130 towards detector 140, and detector 140 measures the intensity of the light at one or more wavelengths. The measurements are provided to controller 150, which analyzes the measurements and provides one or more types of analysis output.

Figure 1B:
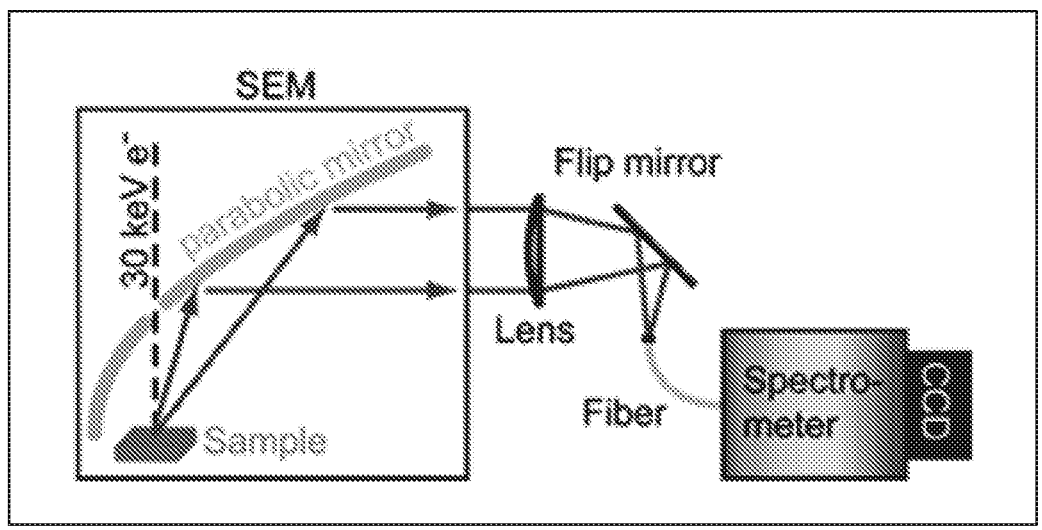
FIG. 1B represents an example of an embodiment of a system for object analysis.

The blocks illustrated in FIG. 1A represent functionality but do not necessarily represent a physical implementation of the functionality. For example, electron beam source 110, sample stage 120, and reflector 130 together may be implemented as a scanning electron microscope (SEM) as illustrated in FIG. 1B, where detector 140 is implemented as a charge coupled device (CCD) spectrometer. As a further example, electron beam source 110, sample stage 120, and reflector 130 may be implemented along with detector 140 and controller 150 in one piece of equipment. Other combinations are also possible, such as detector 140 and controller 150 combined, electron beam source 110 and sample stage 120 combined, reflector 130 and detector 140 combined, or other combination of electron beam source 110, sample stage 120, reflector 130, detector 140 and controller 150.

A block illustrated in FIG. 1A may represent a combination of functionality that is implemented across two or more physical devices. For example, controller 150 may represent multiple processors or multiple computing devices, described below; and reflector 130 may represent multiple mirrors or other reflectors.

Functionality represented by the blocks in FIG. 1A may be omitted, or other functionality introduced into system 100. For example, reflector 130 may be omitted. For another example, lenses, gratings, or diffractors may be introduced (e.g., for filtering or focusing), such as the lens and mirror in FIG. 1B.

Arrows in FIG. 1A represent typical flow of information, but are not limiting. For example, devices implementing functionality of the blocks in FIG. 1A may communicate with each other. In one or more embodiments, devices implementing electron beam source 110 and detector 140 may communicate with each other to automate a CL measurement event.

Sample stage 120 is a platform or receptacle for receiving a sample. In one or more embodiments, a sample may be scanned, meaning that the electron beam follows a path across the sample. In such embodiments, the scan may be performed by moving electron beam source 110 to direct the electron beam along the path, or by moving the sample such that the electron beam follows the path. In the latter case, sample stage 120 includes a mechanical or electromechanical structure for positioning, where positioning may be multi-axis, including but not limited to vertical and horizontal positioning, and tilt positioning. The path of the electron beam may be a line; however, the path may be more complex, and may include, for example, arcs, lines, circles, polygons, and so forth.

Controller 150 represents hardware, firmware, or software, or a combination thereof, which may control portions of system 100. In one or more embodiments, controller 150 directs electron beam source 110; for example, to instruct electron beam source 110 to provide an electron beam, to steer the electron beam, to focus the electron beam, to move the electron beam in a scanning motion, and so forth. In one or more embodiments, controller 150 directs sample stage 120; for example, to instruct sample stage 150 to move horizontally or vertically, or to tilt. In one or more embodiments, controller 150 directs reflector 130; for example, to instruct reflector 130 to move horizontally or vertically, or to tilt. In one or more embodiments, controller 150 directs detector 140; for example, to begin or end measurement, or to take a certain type of measurement (e.g., take measurements within a particular frequency band).

Controller 150 may control one or more of electron beam source 110, sample stage 120, reflector 130 and detector 140 for power management, such as to put devices or functions into a sleep or off state while not in use.

Further, controller 150 may communicate with one or more of electron beam source 110, sample stage 120, reflector 130 and detector 140, such as to receive status updates (e.g., proper operation or maintenance to be scheduled), to retrieve device information (e.g., model number and capabilities), or to receive data (e.g., logs of usage or recorded data).

Controller 150 analyzes data received from detector 140, and provides analysis output in electronic form (e.g., a data file, an image presented on a user interface of a display, or a projected 2D or 3D image) or paper form. Controller 150 may be a computing device. Additionally or alternatively, one or more of electron beam source 110, sample stage 120, reflector 130 and detector 140 may be, or may include, a computing device.

Figure 2:
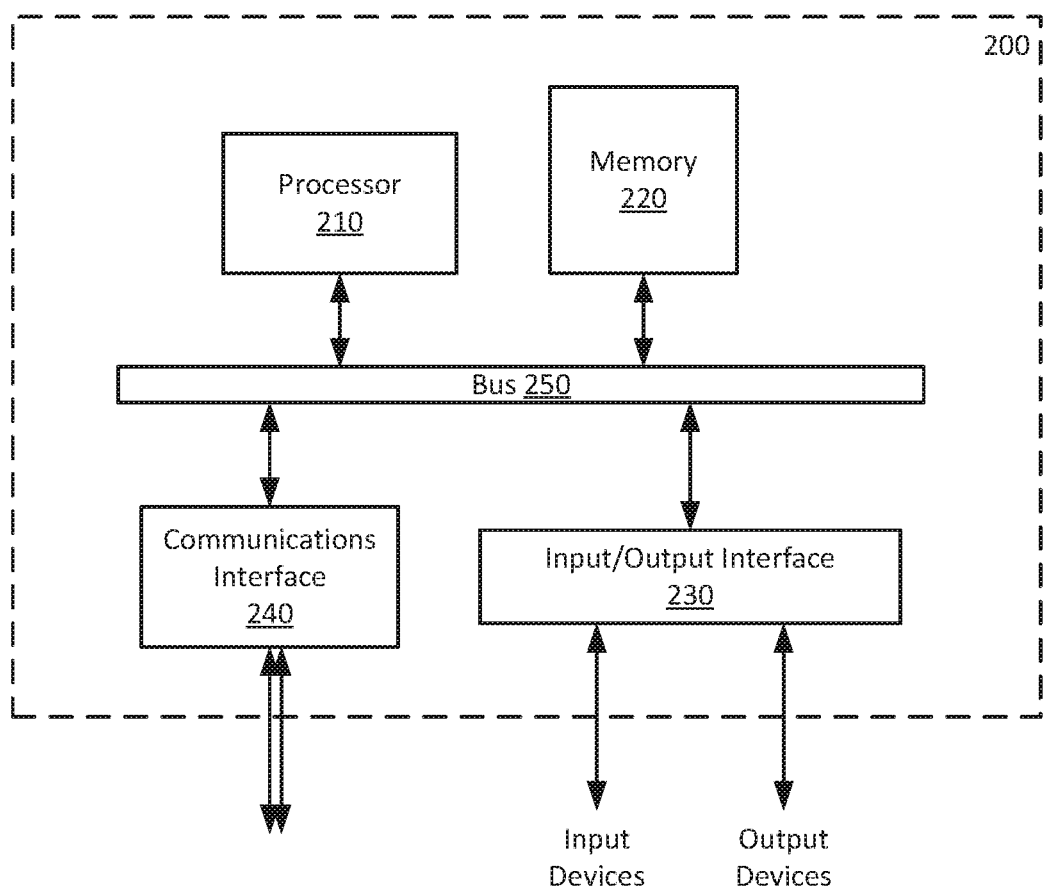
FIG. 2 represents an example of a computing device.

FIG. 2 illustrates an example of a computing device 200 that includes a processor 210, a memory 220, an input/output interface 230, and a communication interface 240. A bus 250 provides a communication path between two or more of the components of computing device 200. The components shown are provided by way of illustration and are not limiting. Computing device 200 may have additional or fewer components, or multiple of the same component.

Processor 210 represents one or more of a general-purpose processor, digital signal processor, microprocessor, microcontroller, application specific integrated circuit (ASIC), field programmable gate array (FPGA), other circuitry effecting processor functionality, or a combination thereof, along with associated logic.

Memory 220 represents one or both of volatile and non-volatile memory for storing information (e.g., instructions and data). Examples of memory include semiconductor memory devices such as EPROM, EEPROM and flash memory devices, magnetic disks such as internal hard disks or removable disks, magneto-optical disks, CD-ROM and DVD-ROM disks, and the like.

Portions of system 100 may be implemented as computer-readable instructions in memory 220 of computing device 200, executed by processor 210.

Input/output interface 230 represents electrical components and optional code that together provide an interface from the internal components of computing device 200 to external components. Examples include a driver integrated circuit with associated programming.

Communications interface 240 represents electrical components and optional code that together provides an interface from the internal components of computing device 200 to external networks, such as a network through which one or more of electron beam source 110, sample stage 120, reflector 130, detector 140 and controller 150 communicate.

Bus 250 represents one or more interfaces between components within computing device 200. For example, bus 250 may include a dedicated connection between processor 210 and memory 220 as well as a shared connection between processor 210 and multiple other components of computing device 200.

An embodiment of the disclosure relates to a non-transitory computer-readable storage medium (e.g., a memory 220) having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as ASICs, programmable logic devices (PLDs), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

The present disclosure describes nanoscale interrogation of optical properties in three dimensions using analysis of CL. CL analysis is referred to herein as CLA. 2D electron-energy loss spectroscopy (EELS) can also be used with tomographic reconstruction; however, while CL and EELS both rely on electron-beam excitation of a sample, they use distinct detection and interpretation techniques. Notably, in one or more embodiments, EELS uses detection of energy lost by electrons transmitted through the sample, whereas CLA uses detection of light emitted by a sample. Thus, CLA allows for higher spectral resolution than is afforded by EELS. Additionally, CLA selectively detects radiative optical processes, whereas EELS indiscriminately probes both radiative and non-radiative processes. Therefore, CLA, unlike EELS, allows direct visualization of the material luminescence and radiative decay of electromagnetic modes.

The high spectral resolution of CLA, along with the selective detection of radiative processes of CLA, could reveal, for example, the regions of highest radiative rate enhancement near a nanostructure, or the distribution of radiative recombination sites in a semiconductor.

In some embodiments, a spectral resolution of the CLA tomographic technique of this disclosure is about 150 nm or less, about 100 nm or less, about 90 nm or less, about 80 nm or less, about 70 nm or less, about 60 nm or less, about 50 nm or less, about 40 nm or less, about 20 nm or less, or about 10 nm or less. In some embodiments, a spatial resolution of the CLA tomographic technique of this disclosure is about 150 nm or less, about 100 nm or less, about 90 nm or less, about 80 nm or less, about 70 nm or less, about 60 nm or less, about 50 nm or less, about 40 nm or less, about 20 nm or less, or about 10 nm or less.

The CLA tomographic technique of this disclosure was demonstrated using a series of maps of a 3D metal-dielectric nanostructure in various orientations. Filtered back-projection was then used to reconstruct intensity, which was correlated with both the material luminescence and radiative LDOS. Owing to the high spatial and spectral resolution afforded by CLA, this reconstruction provides detailed 3D spectral maps of radiative optical properties across visible and near-infrared wavelengths. The techniques described may be extended to infrared wavelengths.

Demonstrations

As described above, CLA may be used to analyze an object. The demonstrations (experimental and simulation) described herein were performed using a particular nanocup design due to features desirable for demonstrating the techniques of the present disclosure. However, it will be apparent to one of ordinary skill in the art that CLA is not limited to the analysis of the particular nanocup, and may also be used to analyze other types, structures and sizes of objects.

Figure 3A:
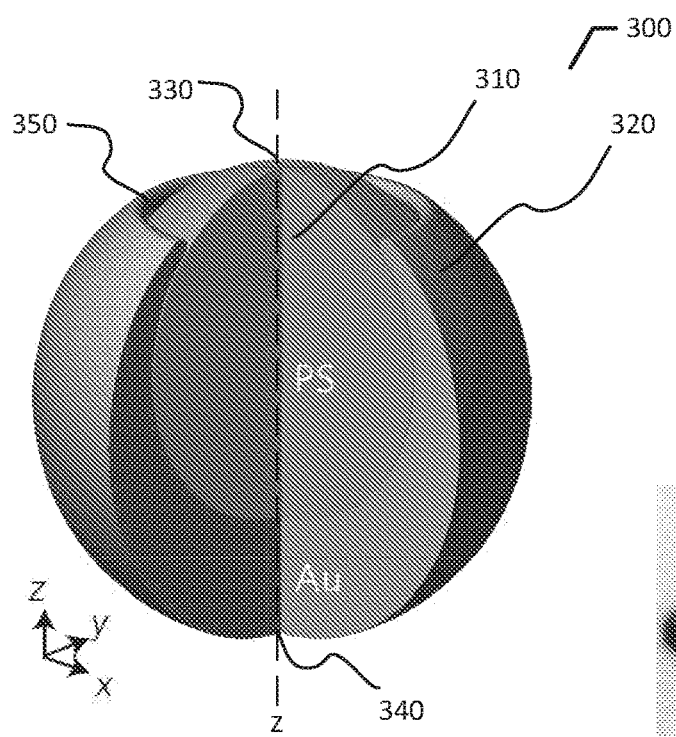
FIG. 3A represents a model of an embodiment of a nanocup.

FIG. 3A illustrates a model of a 3D metal-dielectric plasmonic nanocup 300 used to describe and analyze the CLA techniques of this disclosure. The complex 3D structure of nanocup 300 provides a powerful platform for demonstrating the potential of CLA. Nanocup 300 is composed of a sub-wavelength dielectric core 310 (e.g., polystyrene (PS)), coated with a metallic shell 320 (e.g., gold (Au)). An imaginary axis z is defined from a center 330 of a tip of nanocup 300 to a center 340 of a base of nanocup 300, and defines an axis of symmetry of nanocup 300. As illustrated in FIG. 3A, the dielectric core is offset along the z axis from a center of nanocup 300 such that the dielectric core is exposed from the metallic shell. Thus, there is a tip gap 350 in the metallic shell 320 at the tip of nanocup 300. The model is shown in cutaway form in FIG. 3A for descriptive purpose; however, each of the dielectric core 310 and the metallic shell 320 are symmetric around the z axis in the model.

The nanocup structure illustrated in FIG. 3A has the ability to harvest light over a large bandwidth, confine light on the nanoscale, support electric and magnetic modes, and serve as a constituent of a broadband negative-index metamaterial at optical frequencies.

Optical properties of nanocup 300 include optical properties due to the asymmetry of the core-shell geometry (i.e., the offset of the core along the z axis). The tapered thickness of the metallic shell 320 yields a broadband optical response, while the metallic shell 320 discontinuity across the tip gap 350 provides strong electric and magnetic resonances and field enhancements. However, the rotational symmetry of nanocup 300 imparts it with a degree of insensitivity to polarization as well as relatively facile fabrication.

Figure 3B:
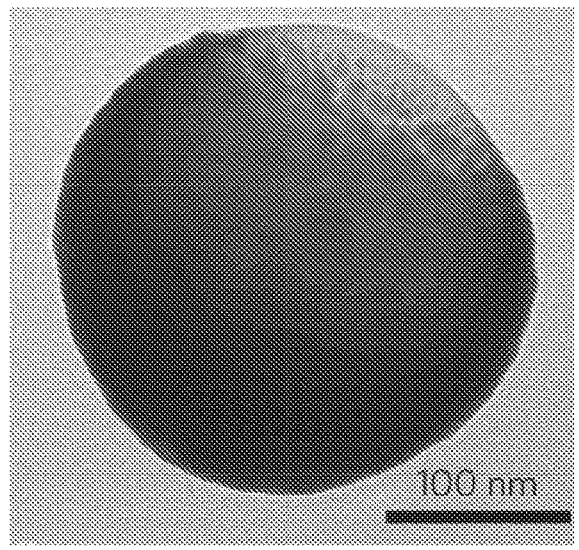
FIG. 3B is an image of an embodiment of a nanocup.
Figure 3C:
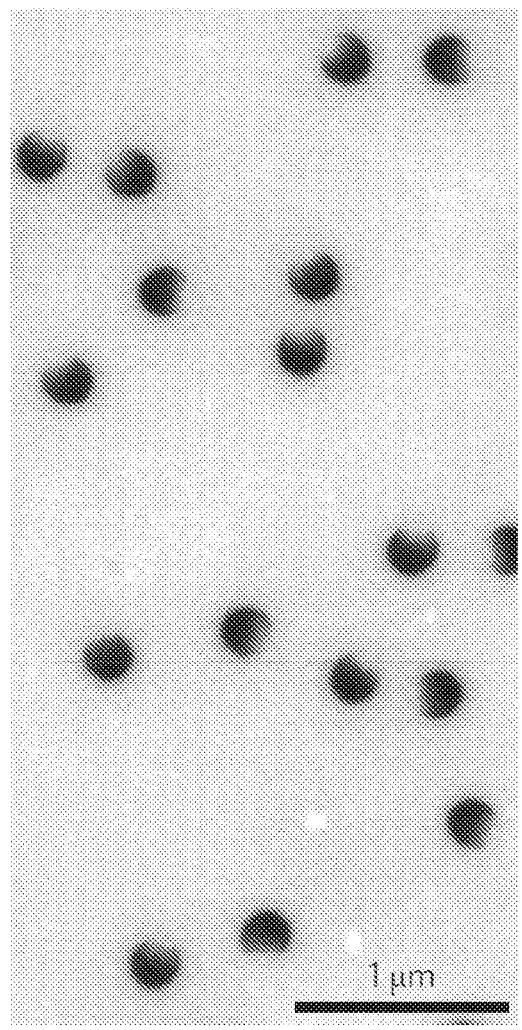
FIG. 3C is an image of multiple nanocups according to an embodiment.

FIG. 3B is a bright-field transmission electron microscopy (TEM) image of a fabricated nanocup, which has the same general structure as the model nanocup 300 of FIG. 3A (i.e., it is a real, non-ideal version of the model). FIG. 3C is a TEM image of multiple manufactured nanocups, illustrating a high degree of uniformity between the manufactured nanocups. FIGS. 3A and 3B reveal the axial symmetry of the individual nanocups The nanocups were fabricated by evaporating gold onto polystyrene spheres.

Figure 4A:
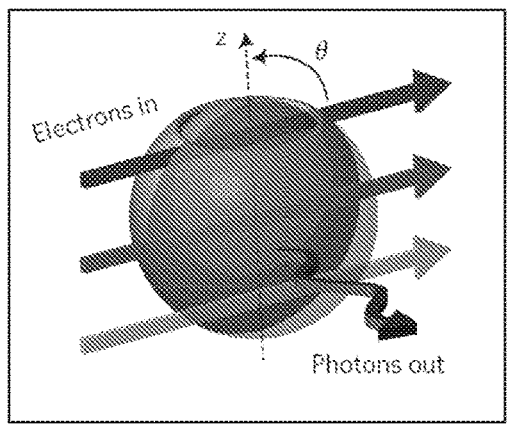
FIG. 4A represents an example of a technique for CL spectroscopy using a scanning electron microscope.
Figure 4B:
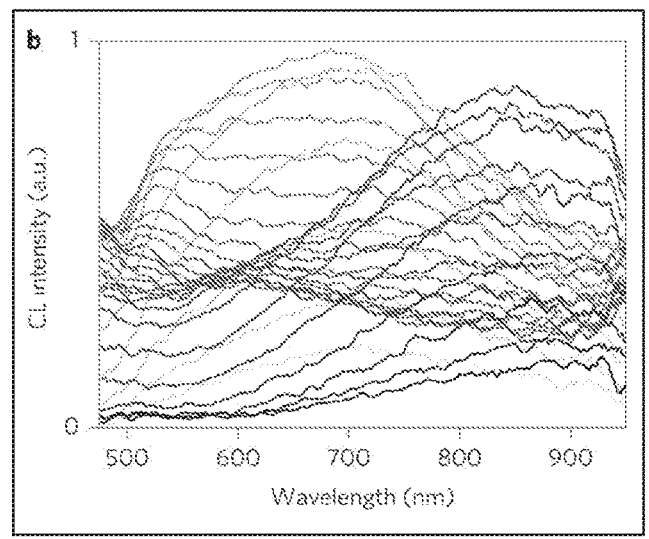
FIG. 4B represents an example of a CL line scan.
Figure 4C:
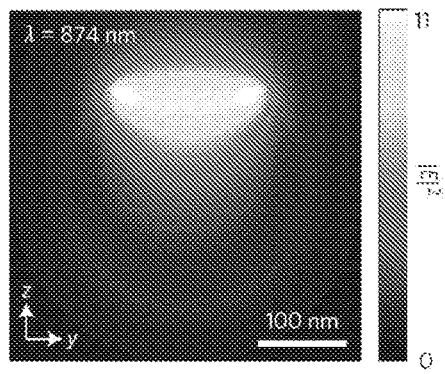
FIG. 4C represents an example of a calculated scattered electric field intensity map.

FIGS. 4A-4B illustrate a technique for CLA spectroscopy using a scanning electron microscope (SEM). FIG. 4A illustrates orientation and respective terminology for the subsequent discussions. The coordinate system rotates with the nanocup such that the z axis is always aligned with the axis of symmetry of the nanocup, and the axis of rotation is defined as the y axis. An incident beam of electrons ("electrons in") is illustrated in FIG. 4A for various positions along the z axis. An incident beam is applied at an angle θ to the axis of symmetry z of the nanocup. An angle of θ=0° corresponds with an alignment of the incident beam with the z axis. As the incident electron beam is applied to the nanocup, photons are emitted ("photons out"), and intensity of the emitted photons is measured. FIG. 4B shows a result of scanning an electron beam along the z axis through the center of a nanocup oriented at an angle of 90° (e.g., the orientation illustrated in FIG. 4A). Darker lines in FIG. 4B correspond to darker lines for the incident beam position in FIG. 4A. At the tip of the nanocup (at the top of FIG. 4A in the orientation shown), there is a peak of intensity at a wavelength of approximately 850 nm, representing resonance of the nanocup at a low energy. The low-energy resonance of the nanocup is characterized by strong electric field enhancement near the tip of the structure, referred to herein as the tip mode. This has been confirmed by finite-difference time-domain (FDTD) simulations. FIG. 4C illustrates scattered electric field intensity in a cross-section of the nanocup, calculated by FDTD simulations for excitation with an x-polarized plane wave propagating in the −z direction at a wavelength of 874 nm (the peak in the extinction efficiency). More detail of the FDTD analysis is provided below with respect to FIG. 10. The spatial and spectral characteristics of the tip mode have also been confirmed by numerical simulations of CL using a BEM technique, as will be described in detail below with respect to FIG. 12.

As the electron beam continues the scan and passes through the base of the nanocup (at the bottom of FIG. 4A in the orientation shown), there is a broad peak of intensity between approximately 550 nm and 700 nm. There are at least three contributing factors to the broadness of the peak: the high-energy plasmonic resonance supported by the nanocup, the contribution of radiation from electron-hole pair recombination in the gold shell, and luminescence from the polystyrene core of the nanocup. The higher-energy plasmonic modes exhibit significant field intensity near and inside the base of the nanocup, as discussed below. However, BEM CL simulations reveal that radiative decay of the high-energy modes alone cannot account for the strong signal at short wavelengths. By comparing CL spectra to photoluminescence (PL) spectra of both nanocups and polystyrene cores, it can be seen that a significant portion of the CL intensity at short wavelengths is due to gold and polystyrene luminescence. (See additional detail with respect to FIGS. 11A-11E).

Figure 4D:
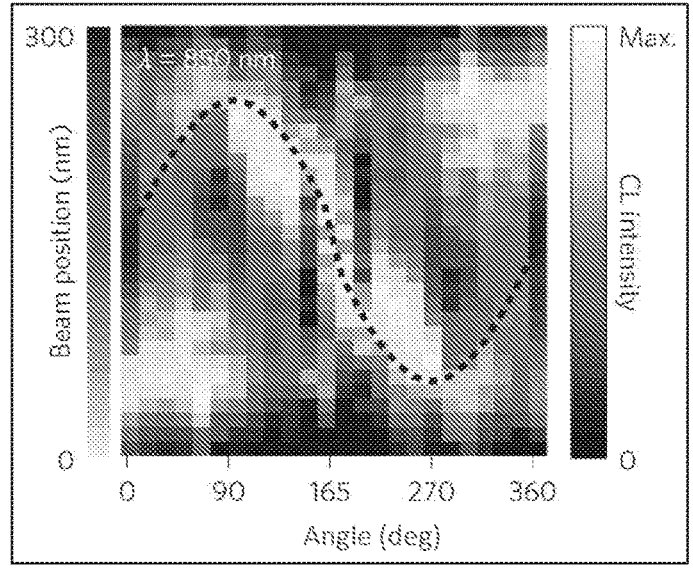
FIG. 4D represents an example of a sinogram.

To analyze the effect of nanocup angle on CL excitation efficiency, CL line scans were collected for various nanocups at angles between 0° and 165°, in 15° increments. The normalized CL intensities at 850 nm were used to form a sinogram, shown in FIG. 4D. In the sinogram, data from 0° to 165° is flipped and repeated for angles of 195° to 360° due to the reflection symmetry of the nanocup (a nanocup positioned at 180° was not available). The dashed-line overlay denotes the physical position of the center of the nanocup tip gap, derived from the nanocup model. From this sinogram, it was determined that the tip mode at a wavelength of 850 nm is excited for most nanocup angles, except for a few angles near 0° and 180°. At 0° and 180°, the orientation of the electron beam results in inefficient excitation of the tip mode, as the electron beam preferentially couples to out-of-plane electric-field components.

Figure 4E:
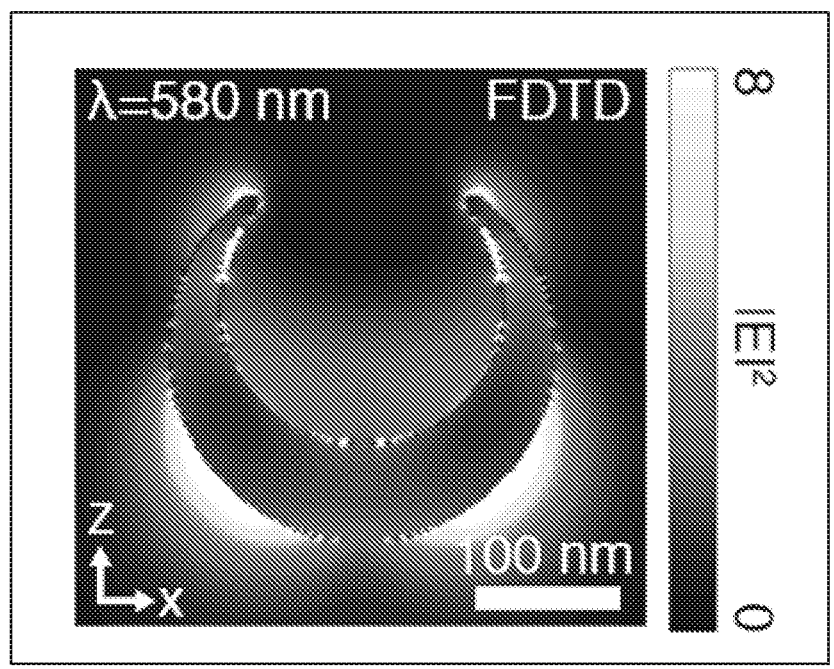
FIG. 4E represents an example of a central cross-section analysis of the intensity of a scattered electric field.

FIG. 4E illustrates a central cross-section analysis of the intensity of the scattered electric field for a plane wave incident along −z and polarized along x, at a wavelength of 580 nm. The largest enhancement is concentrated near the base of the nanocup at this wavelength.

Figure 4F:
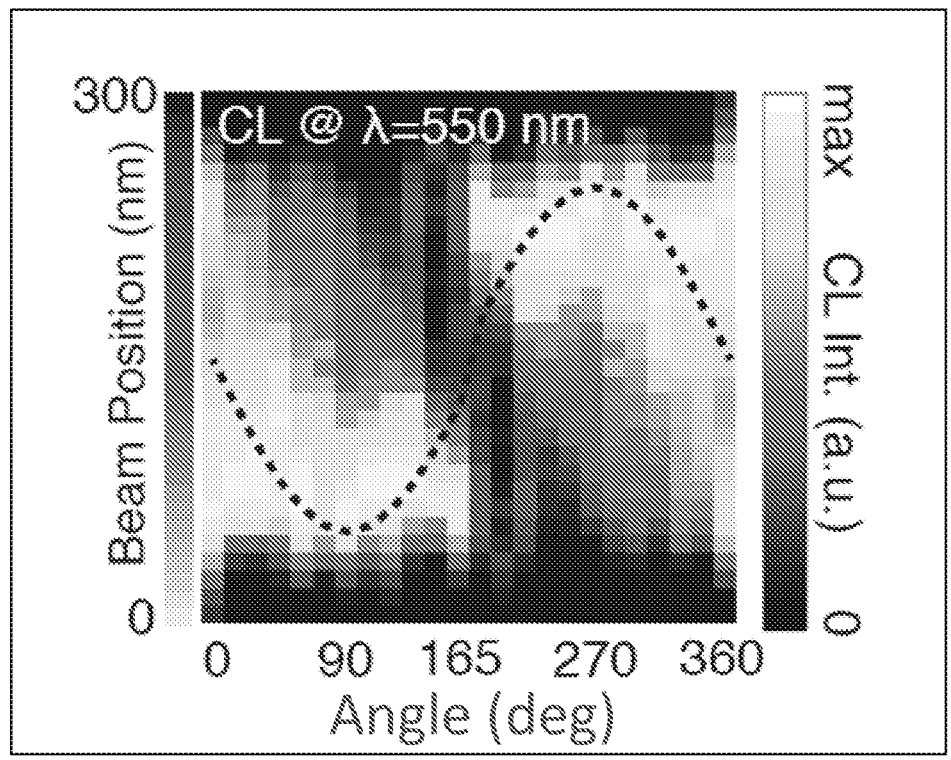
FIG. 4F represents an example of a sinogram.

FIG. 4F illustrates a sinogram of central cross-section CL scans at 550 nm for a variety of angles, showing that CL is excited efficiently near and in the base of the nanocup over a broad range of angles, as expected. The dashed line tracks the position of the center of the base of the nanocup.

Figures 5A, 5B, 5C:
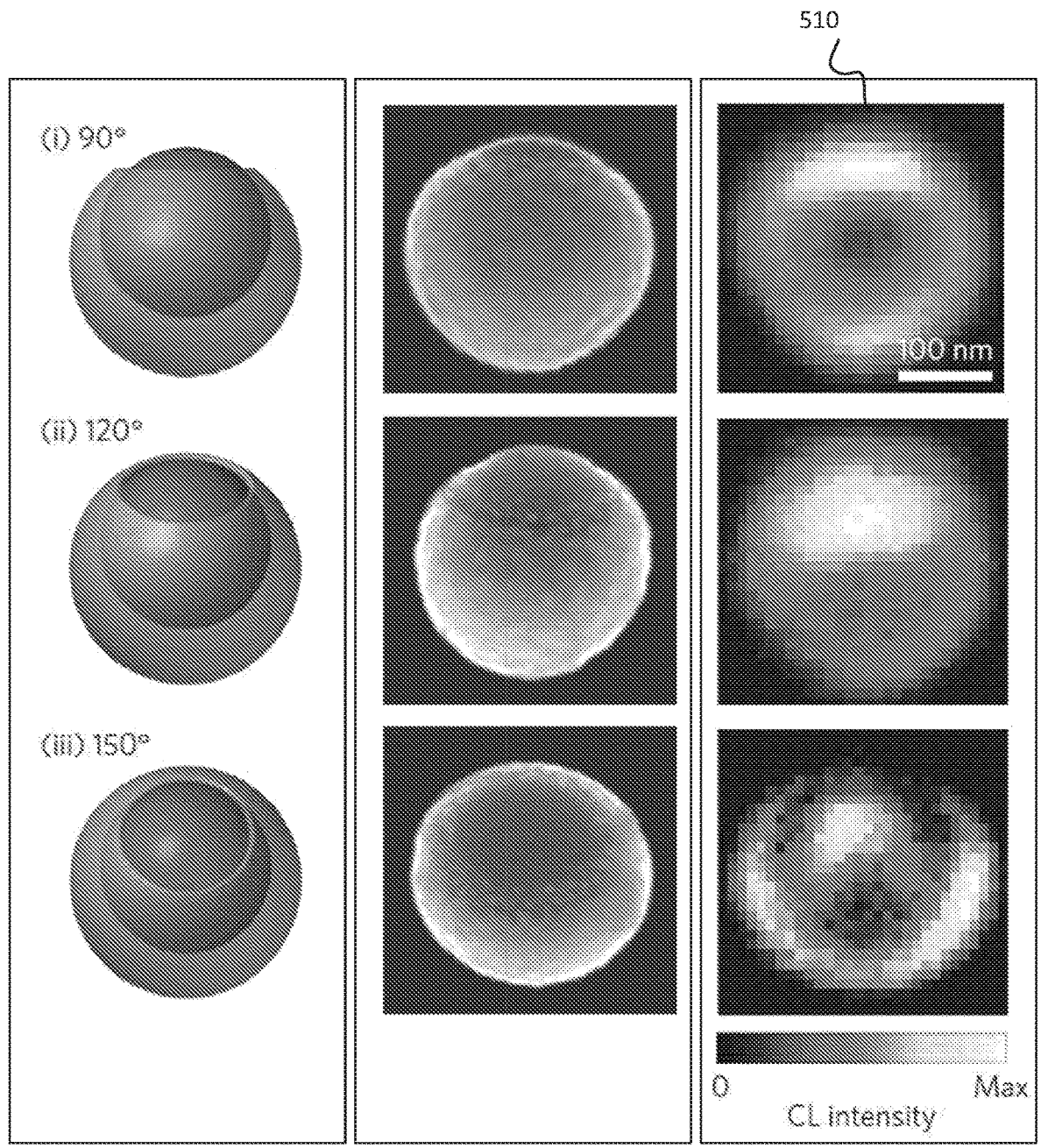
FIG. 5A represents a model of a nanocup oriented at three different angles.
FIG. 5B and FIG. 5C represent respectively examples of scanning electron microscope images and corresponding 2D maps of normalized CL intensity for the three nanocup orientations of FIG. 5A.

FIGS. 5A-5C illustrate the results of using SEM beam scanning, collecting a spectrum at each position, and generating 2D CL maps. FIG. 5A illustrates models of three nanocup orientations, at 90°, 120° and 150°. FIG. 5B illustrates SEM images of three nanocups positioned at the respective three orientations of FIG. 5A. FIG. 5C illustrates 2D maps of normalized CL intensity of the respective nanocups of FIG. 5B at a wavelength of 850 nm. Note that the 2D CL maps in FIG. 5C are extensions of the one-dimensional line scans compiled in the sinogram of FIG. 4D. The 2D CL maps in FIG. 5C confirm that various modes can be excited for a wide range of nanocup angles, allowing for 2D tracking of radiative optical properties for wavelengths spanning the visible and near-infrared spectrum.

Figures 6A, 6B, 6C, 6D:
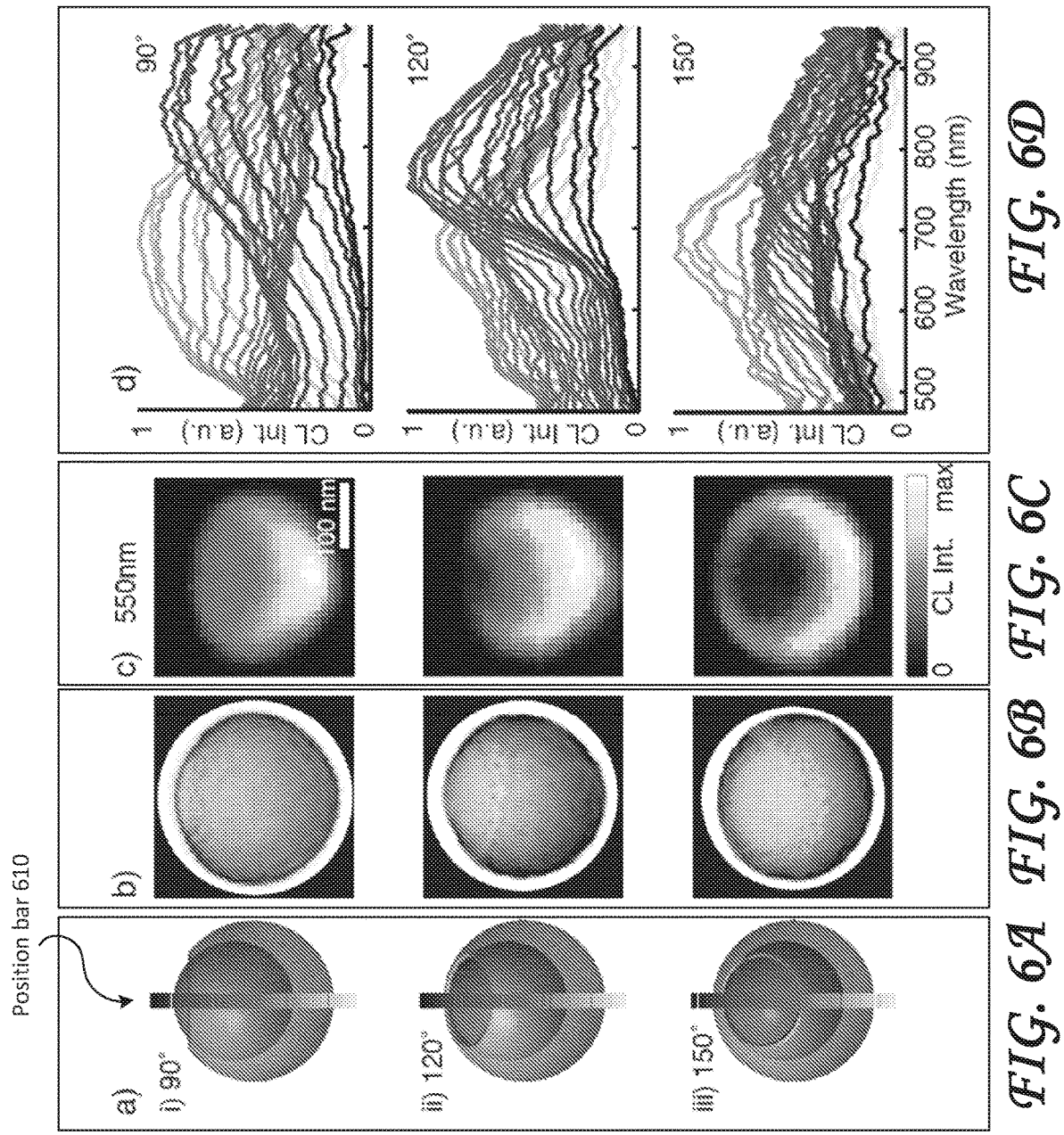
FIG. 6A represents a model of a nanocup oriented at three different angles.
FIG. 6B, FIG. 6C and FIG. 6D represent respectively examples of scanning electron microscope images, corresponding 2D maps of normalized CL intensity, and CL line scans for the three nanocup orientations of FIG. 6A.

FIGS. 6A-6D illustrate results of another SEM beam scan for three orientations of nanocups (at 90°, 120° and 150° as illustrated in FIG. 6A). In FIG. 6A, a position bar 610 at each orientation indicates beam position by gradation, for comparison to the graphs of FIG. 6D, with dark lines at the tip of the nanocup in the orientation shown progressing to lighter lines at the base of the nanocup. FIG. 6B illustrates SEM images of nanocups positioned as shown in the respective orientations in FIG. 6A. FIG. 6C illustrates respective 2D maps of normalized CL intensity, and FIG. 6D illustrates respective CL line scans, where darker lines indicate incident beam position at the tip of the nanocup (corresponding to the darker portion of the position bar 610 shown for the respective orientations).

CL maps represent 2D projections of a 3D function. Tomography is used to reconstruct a 3D function from a 2D CL map, and thereby map the CL intensity in 3D. In CLA, the intensity of a given pixel in a 2D map (e.g., the maps in FIG. 5C or FIG. 6C) is proportional to an integral of the CL intensity along a path of an electron.

Prior to describing CLA 3D reconstruction mapping, TEM 3D reconstruction mapping is first discussed by way of comparison. For both CLA and TEM reconstructions, the generated images should satisfy the projection requirement (e.g., be linear and monotonic with the property of interest). The intensity of a TEM image is related to the integrated thickness and atomic number of the constituent materials, and satisfies the projection requirement. TEM reconstruction was performed for a nanocup oriented at 90° (e.g., the orientation shown in FIG. 4A). With this orientation, the axis of rotational symmetry z of the nanocup is perpendicular to the incident electron beam. As the nanocup is (substantially) rotationally symmetric, a single TEM projection can be used as a virtual tilt series spanning 360° of rotation. To reconstruct the nanocup structure, the tomographic technique of filtered back-projection was used, which forms a reconstructed image by summing partial reconstructions at various angles. This technique is described in more detail below.

Figure 7A:
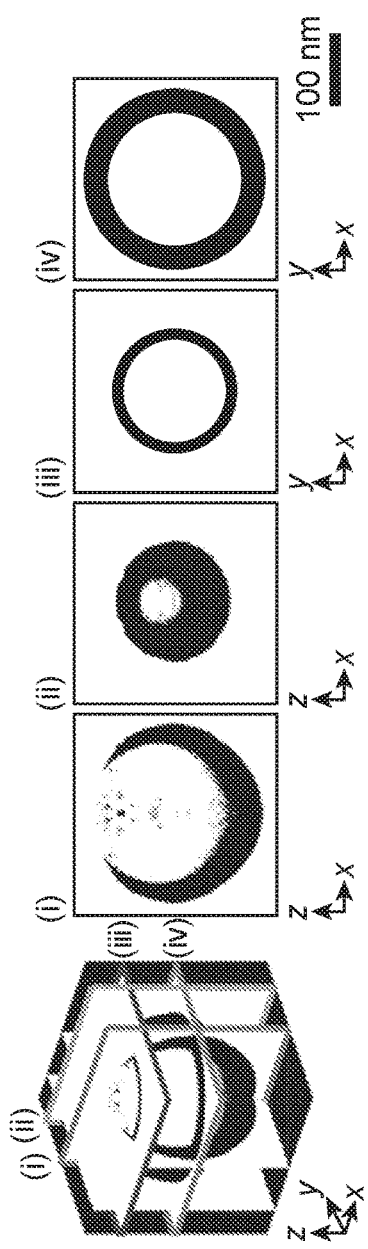
FIG. 7A represents an example of a transmission electron microscope tomographic reconstruction.

FIG. 7A illustrates a TEM tomographic reconstruction. The black portions of the reconstruction correspond to regions of high atomic number (e.g., gold), whereas the dielectric core appears white, similar to the vacuum background. In FIG. 7A, panels (i) to (iv) correspond to different cross-sections through the reconstruction. Panel (i) is an x-z cross-section of the reconstruction at the midpoint of the nanocup; panel (ii) is an off-center x-z cross-section of the reconstruction; panel (iii) is an x-y cross-section of the reconstruction at an upper z position; and panel (iv) is an x-y cross-section of the reconstruction at the midpoint of the nanocup, showing the metallic shell surrounding the inner core. Comparing this 3D tomogram of FIG. 7A with the TEM image in FIG. 4B, it can be seen that reconstruction provides a significantly improved spatial representation of the structure.

Next, two different techniques for CLA 3D reconstruction are discussed: (1) a virtual tilt series constructed from a single experimental projection utilizing the rotational symmetry of a single nanocup and (2) an experimental tilt series of nanocups.

For the virtual technique, the 2D CL map of FIG. 5C for the 90° orientation (map 510) was used as a virtual tilt series spanning 360° of rotation. For this nanocup, oriented at 90° with respect to the electron beam, the excited modes are (ideally) the same for any angle of rotation of the nanocup about the z axis due to the rotational symmetry of the nanocup. While modes that specify a z-oriented electron beam are not excited in this configuration, the trajectory dependency of the excitation of other modes is eliminated, as they will contribute uniformly to the CL across all tilt angles, allowing for a scalar reconstruction. This use of symmetry simplifies an otherwise complex vector tomography problem. Additionally, material luminescence is a scalar quantity and thus independent of trajectory (within the small particle assumption), and therefore satisfies the projection requirement. Thus, the single nanocup oriented at 90° is used for a virtual tilt series to directly reconstruct all but the z component of the CL using scalar tomographic techniques. Note that this assumes negligible particle-substrate interactions, a reasonable assumption for a nanocup at $\theta=90°$ (see the discussions related to FIGS. 16 and 17).

Figure 7B:
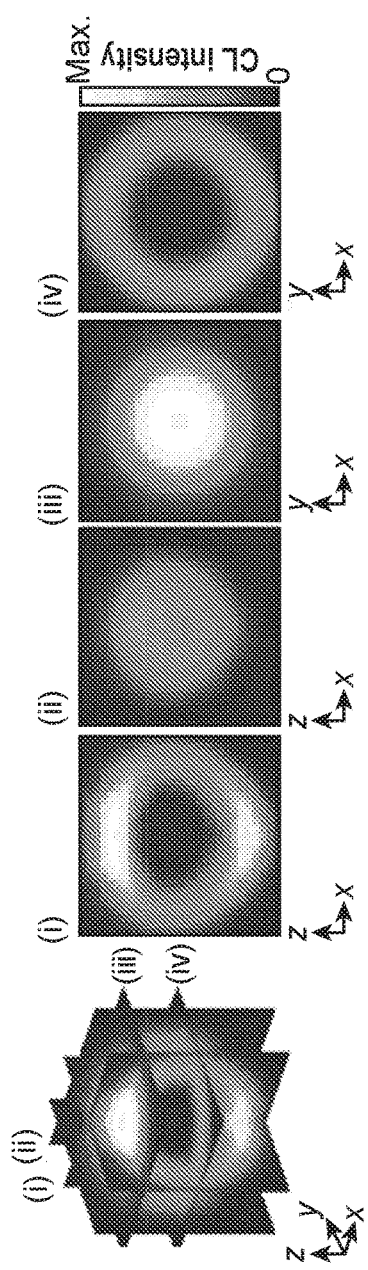
FIG. 7B represents an example of a 2D tomographic reconstruction of a 2D CL map.
Figure 18:
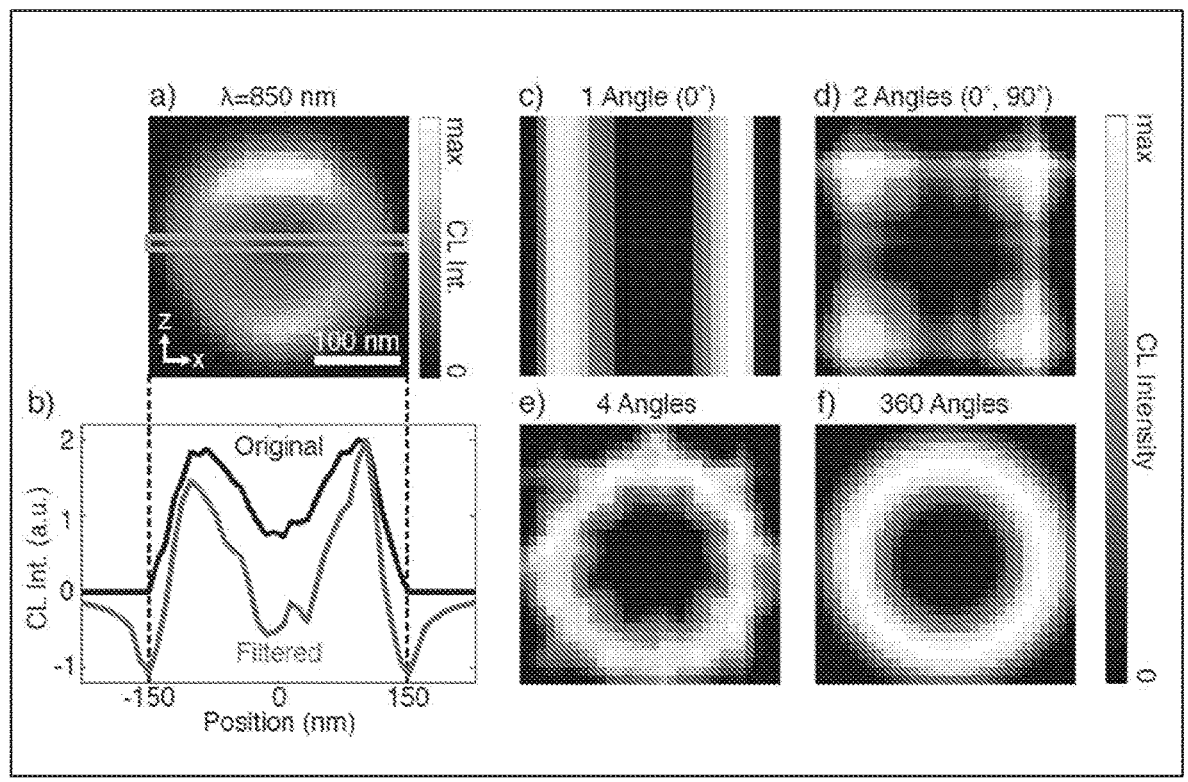
FIG. 18 represents examples of reconstruction of CL by a filtered back projection technique.

FIG. 7B illustrates a 3D tomographic reconstruction of the 2D CL map 510 of FIG. 5C at a wavelength of 850 nm using the virtual technique (see also the description related to FIG. 18). Based on symmetry of the nanocup in the 90° orientation, a horizontal slice across 2D CL map 510 may be used to represent the nanocup along the entire x-y plane that includes the slice. Thus, multiple slices at different z levels may be used describe different x-y planes of the nanocup, and thereby reconstruct a 3D CL tomogram from the x-y planes. As seen in FIG. 7B, the highest intensity of CL at this wavelength is localized within the nanocup tip gap; panels (i) and (iii) in particular illustrate the strong field enhancements that are spatially localized in z near the tip of the nanocup. This localization of CL intensity is expected for the tip mode based on the FDTD simulations shown in FIG. 4C, as well as BEM simulations (see also the discussion related to FIG. 12). Referring still to FIG. 7B, significant CL intensities can also be observed near and around the metallic shell, mostly from the luminescence of the gold itself.

For the experimental tilt series technique to approximate a reconstruction of the complete CL including modes excited in the three orthogonal directions, a tilt series is analyzed, in which the angle between the electron beam and the z axis of the nanocup is varied. The angular dependence of the excitation of the various modes does not strictly satisfy the projection requirement, so the range of angles considered was restricted in some experiments to minimize or reduce an effect of angular dependence. In one or more embodiments, the tilt series is normalized at each wavelength before reconstruction, to minimize or reduce an effect on the reconstruction of variation in excitation efficiency. The resulting tomogram provides useful information about the existence and qualitative 3D distribution of excitable modes in the structure under consideration.

Figure 7C:
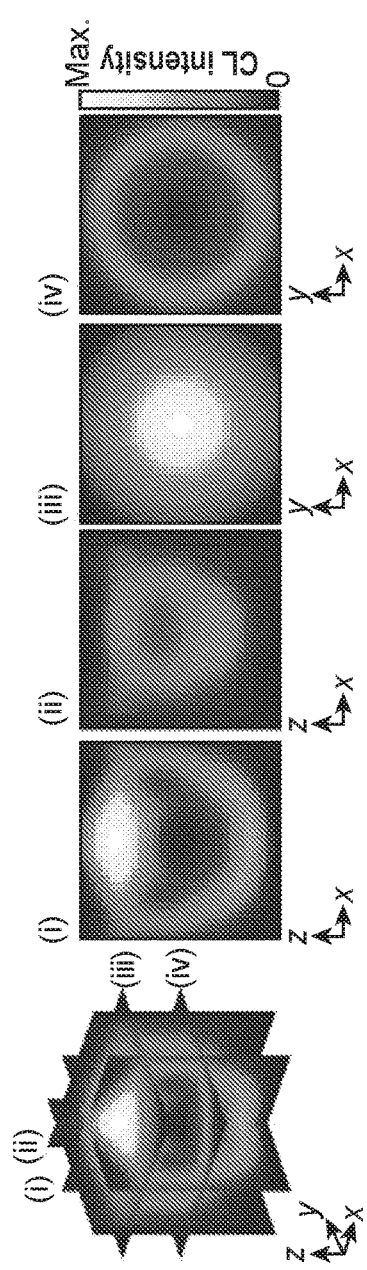
FIG. 7C represents a 2D reconstruction of CL based on reconstructing individual x-z planes.
Figure 7D:
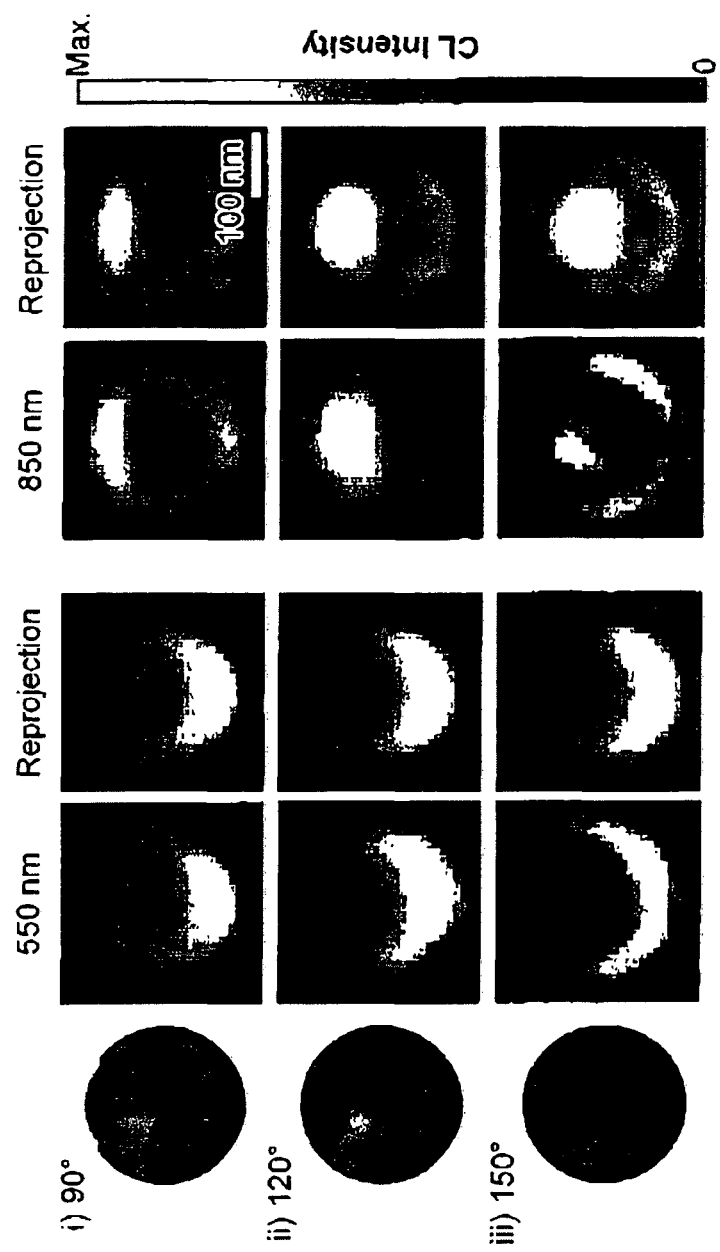
FIG. 7D represents a comparison of reconstructions to re-projections.

In one experiment using the tilt series technique to reconstruct a 3D CL tomogram, 2D CL maps were obtained for nanocups with angles between 75° and 165°, in 15° increments (which, due to the reflection symmetry of the nanocups, are substantially equivalent to the 2D CL maps for angles between 195° and 285°). These particular angles were selected in this experiment because particle-substrate interactions are negligible at these nanocup orientations. Reconstruction of the 3D CL tomogram was performed using a filtered back-projection technique, by 2D reconstruction in the x-z plane for each value of y, imposing symmetry during reconstruction to enhance the quality of the tomogram. FIG. 7C illustrates a 3D reconstruction of the CL at a wavelength of 850 nm based on reconstructing individual x-z planes. This experimental multi-nanocup reconstruction compares well with the reconstruction from the single projection in FIG. 7B: the strong field enhancement near the tip shown in both panels (i) and (iii), the reduced areal cross-section in (ii), and the intensity in and around the gold shell in (iv). The agreement between the two reconstruction technique results (e.g., as illustrated in FIGS. 7A and 7B), based on two very different sets of initial data, indicates both the validity of the assumption of negligible particle-substrate interactions for the angles considered here, as well as the merits of the reconstruction scheme. The quality of the multi-nanocup reconstruction was also confirmed by comparing the original CL maps to re-projections of the tomograms at the same angles, as provided in FIG. 7D, which is a side-by-side comparison of 2D CL maps to re-projections of the tomograms, at 550 nm and 850 nm wavelengths.

Figure 8A:
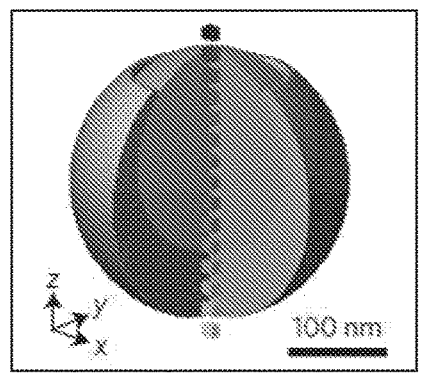
FIG. 8A represents a model of a nanocup.
Figure 8B:
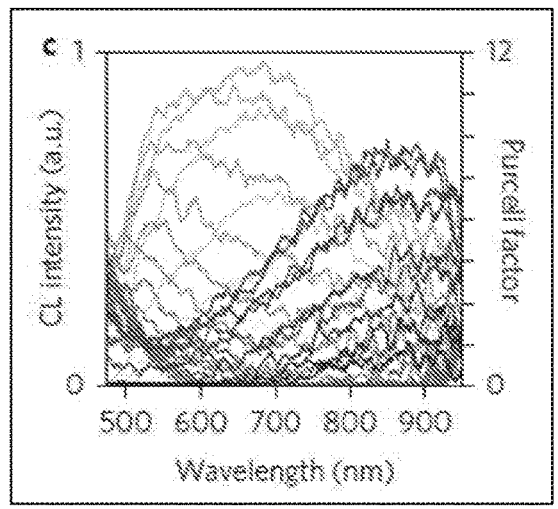
FIG. 8B represents a CL line scan.
Figure 8C:
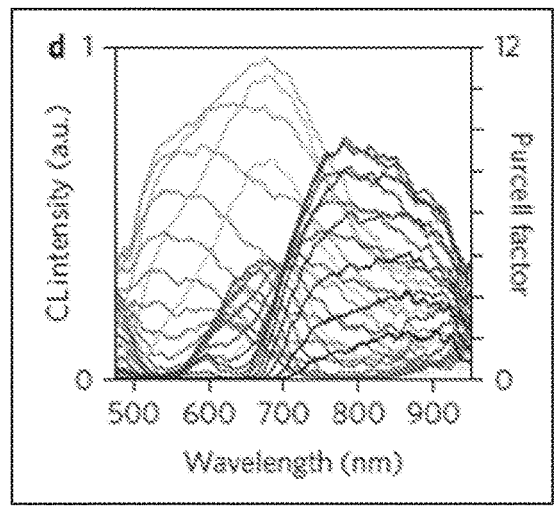
FIG. 8C represents a CL line scan.

Because CLA is a spectroscopic technique, the CL may be reconstructed in 3D at all wavelengths in the measured 475-950 nm range. FIGS. 8A-8D are illustrative. FIG. 8A illustrates a nanocup at a 90° orientation, with volumetric pixels, or voxels, along the central axis of the nanocup. The voxels are shown in gradation from darker to lighter, corresponding to the gradations of lines in FIGS. 8B-8D. FIG. 8B shows associated spectra for a single-nanocup CLA reconstruction, and FIG. 8C shows associated spectra for a multi-nanocup CLA reconstruction. By comparing these spectra with the gradated voxels in FIG. 8A, it can be seen that the CL spectra vary significantly with position. Near the metallic base of the nanocup (lightest gradation), the CL intensity peaks broadly between 550 nm and 700 nm; in the dielectric near the tip of the nanocup (darkest gradation), the CL intensity peaks again, at approximately 800 nm to 850 nm. Aside from the discrepancy between the spectra in the dielectric core of the nanocup, which will be discussed below, the main spectral trends are visible in both the single- and multi-nanocup reconstructions.

Figure 8D:
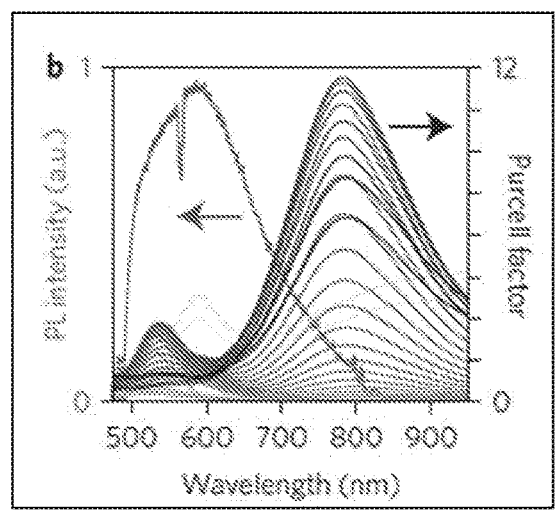
FIG. 8D represents a comparison of Purcell factor to photoluminescence intensity.
Figure 20:
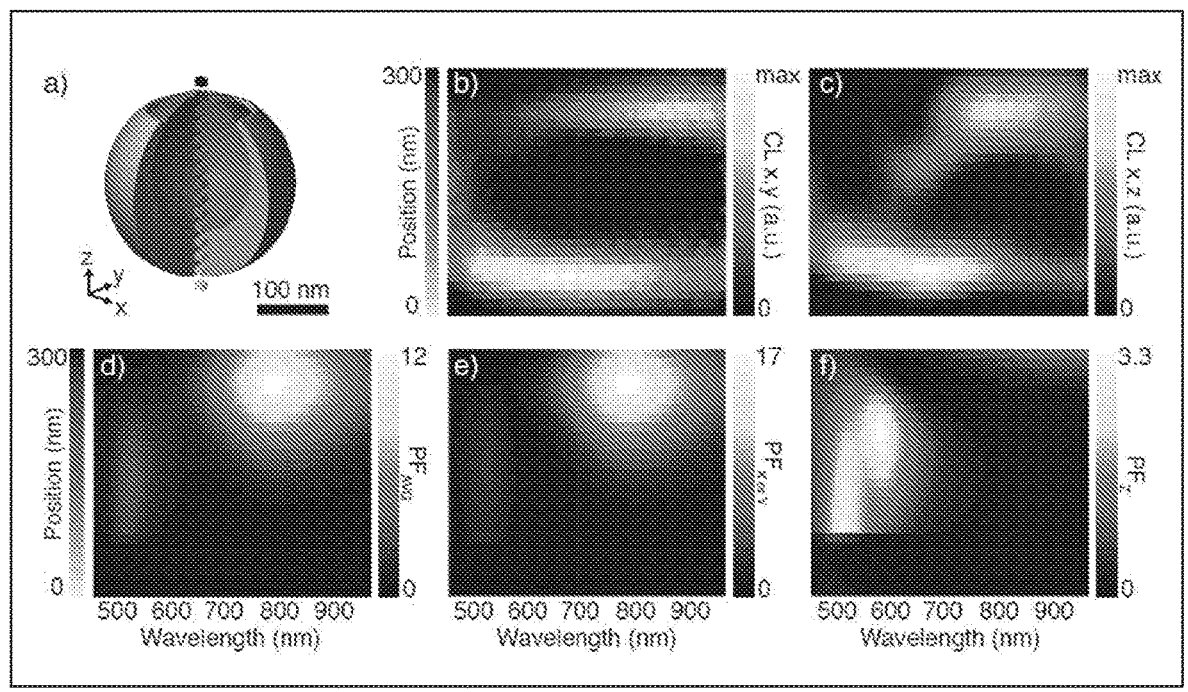
FIG. 20 represents examples of reconstructed CL spectra at voxels along a central axis of a nanocup for single- and multi-nanocup reconstructions.

The spatial dependency of the CL can be understood by considering two factors contributing to the intensity of the CL: the radiative LDOS within the nanocup structure and luminescence from the gold and polystyrene. To investigate the radiative LDOS, which is a measure of the number of radiative decay pathways available to an emitter, an FDTD technique was used to calculate the radiative rate enhancement, or Purcell factor (PF), at each position along the nanocup axis. FIG. 8D plots a total PF (average of x, y and z components) calculated with FDTD (PF on the right vertical axis, and PF curves having peaks on the right side), and average PL spectra of six individual nanocups excited at 488 nm (PL on the left vertical axis, and the PL curve having a peak on the left side). The calculated total PF (shown in FIG. 8D) indicates that the radiative LDOS peaks in the tip gap region of the nanocup at a wavelength of 782 nm. This calculated result is in good agreement with the peak seen in the same spatial region in the reconstructed CL spectra of FIGS. 8B and 8C. The rapid fall in signal intensity for voxels farther away from the tip is also similar in the calculated PF spectra and the experimental CL spectra (see also the discussion related to FIG. 20).

Near the metallic base of the nanocup, the reconstructed CL exhibits a significant and broad peak between 500 nm and 700 nm, which is not fully reproduced in the calculated PF spectra. This feature is also absent from BEM CL calculations discussed below with respect to FIG. 12. Like the BEM calculations, the PF calculations do not account for material luminescence and, indeed, PL measurements of individual nanocups reveal significant electron-hole pair recombination in the gold shell, as shown in FIG. 8D. The PL from the gold shell peaks at a wavelength of 593 nm, with a spectral shape that closely resembles the reconstructed CL. The narrower width of the PL spectrum may be due to the narrowband characteristic of the laser used for PL experiments (compared to the broadband nature of the electron beam as an excitation source in CLA) or to the different temporal characteristics of the excitation. Also, note that the spike at 568 nm is related to the dominant Raman line (—$CH_3$ symmetric stretch, 2,886/cm) of the polydimethylsiloxane (PDMS) substrate used in the PL experiment.

In the dielectric core of the nanocup, the multi-nanocup reconstruction (FIG. 8C) reveals a peak at approximately 650 nm not present in the single-nanocup reconstruction (FIG. 8B). This peak is due to a mode that is not efficiently excited at 90° and therefore does not show up in the single-nanocup reconstruction, which ignores modes that specify a z-oriented electron beam for efficient excitation. This mode is confirmed through plane-wave extinction calculations, BEM CL simulations, and PF calculations, confirming the existence of a mode at approximately 600 nm excited in the center of the nanocup for a z-oriented dipole, but not for x- or y-oriented dipoles, as described in more detail below (see also the discussion related to FIGS. 10 and 21). The existence of this peak in the CLA tomogram demonstrates the ability of the multi-nanocup reconstruction to probe the many modes of the system. It is interesting to note that the spectra of both reconstruction techniques show significant CL in the dielectric core of the nanocup below 500 nm. This CL stems from the luminescence of the polystyrene bead itself, which peaks at about 450 nm (see the polystyrene PL spectrum in FIG. 11E).

As can be seen from FIGS. 8B-8D and the related discussions, the CLA reconstructions demonstrate high spatial and spectral resolution.

Figure 9:
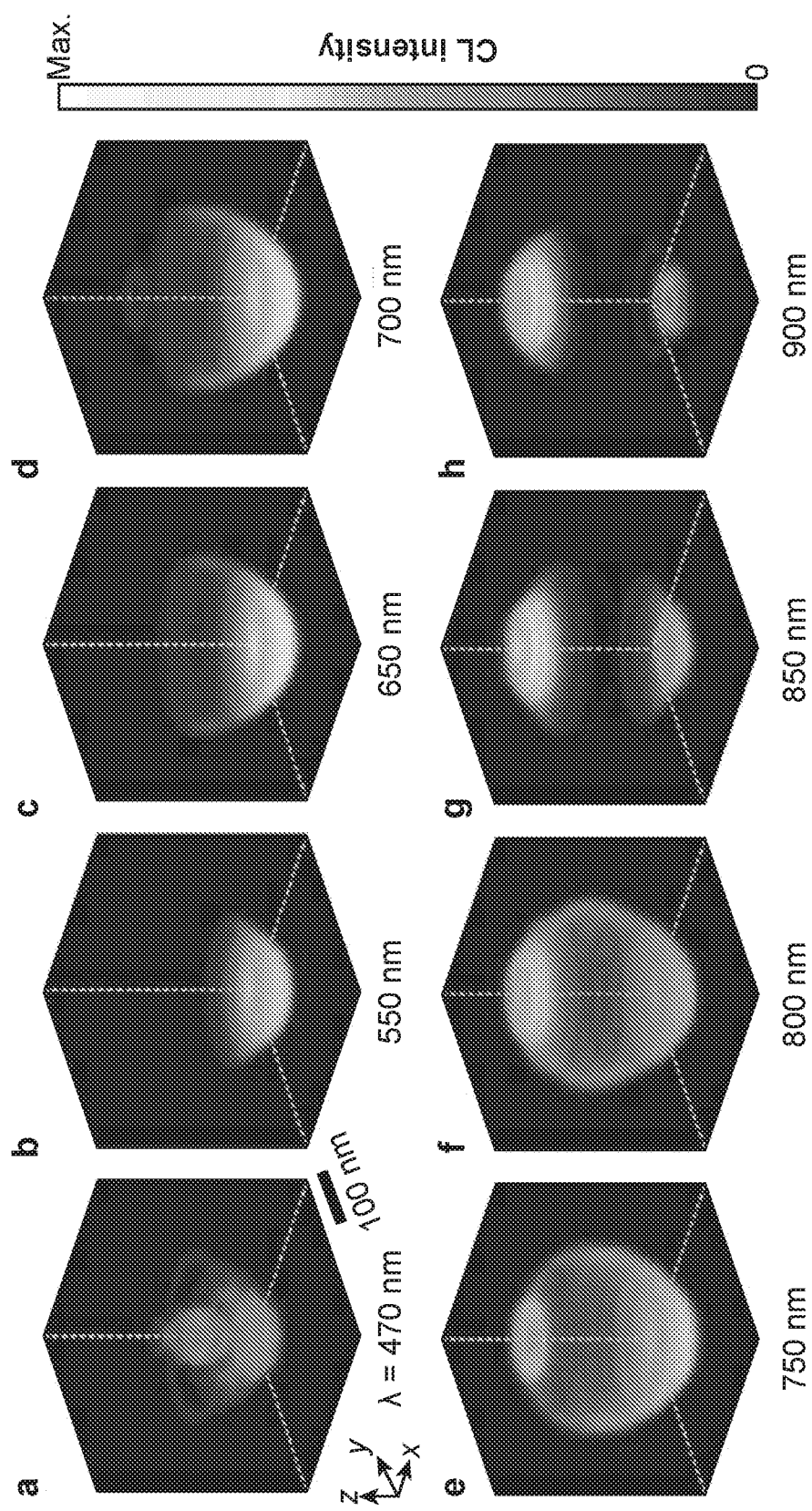
FIG. 9 represents an example of spectral and spatial dependence of CL.

FIG. 9 is illustrative of the spectral and spatial dependence of the CL, presenting 3D CLA reconstruction tomograms at eight different wavelengths between 470 nm and 900 nm, for a single nanocup at 90° (where the nanocup tip gap is positioned at the top of the figures). The spectroscopic CLA tomograms of FIG. 9 demonstrate how different spectral features contributing to the CL spectrum of a 3D nanostructure can be resolved at a spatial resolution well below the diffraction limit.

Thus has been described CLA spectroscopic tomography techniques that allow for probing deeply sub-wavelength radiative optical properties in three dimensions. The technique allows spectral reconstruction of individual nanoscale volumetric pixels, spanning visible and near-infrared frequencies. The resultant tomograms reveal regions of efficient CL, with contributions from both material luminescence and radiative decay of resonant electromagnetic modes. It should be understood that the analysis results provided are not limiting on the technique: CLA tomographic reconstructions that include momentum-resolved and polarization-resolved information with nanometer-scale voxel resolution are contemplated. Further, the application of CLA tomography as described in this disclosure is not limited to analysis of small structures such as the described nanocup, but is directly applicable to analyses of far more complex and/or far larger systems. For example, this tomographic technique could be used to precisely locate radiative recombination centers in light-emitting diodes, probe the nanoscale distribution of defect states in organic photovoltaics, and provide new label-free avenues for biological imaging.

Materials, Equipment and Setup

Nanocups were fabricated by metal evaporation onto dielectric beads. An aqueous solution of 200-nm-diameter polystyrene beads (Polysciences, coefficient of variance=8%) was deposited onto a glass coverslip coated with polydiallydimethylammonium chloride, a charged polymer used to improve areal coverage. The coverslip was then mounted on a rotation stage tilted at an angle of approximately 45° and rotated at 45 rpm during electron-beam evaporation. Gold was evaporated at a rate of approximately 1 Angstrom/second until the thickness of the metal at the base of the dielectric beads reached approximately 70 nm. For TEM imaging, the nanocups were removed from the substrate with a carbon grid coated with an ultra-thin layer of PDMS. For CLA experiments, the nanocups were removed from the original substrate with a PDMS stamp and then transferred onto a clean silicon wafer via a transfer printing procedure that did not preserve their orientation. The orientation of each nanocup was determined by taking SEM images at a stage tilt of 0° and 40°, and the images were compared to a computer-generated tilt series.

TEM images were obtained using an FEI Tecnai G2 F20 X-TWIN TEM at 200 keV in bright-field imaging mode.

CL measurements were performed in an FEI XL-30 SFEG SEM with an aluminum paraboloid mirror attached to a piezoelectric positioning system. A 30 keV electron beam passed through a 600 μm hole in the mirror, directly above its focal point. The beam spot diameter was approximately 10 nm and the typical beam current used was approximately 1 nA. Emitted radiation was collected by the mirror and passed outside the microscope into a spectrometer fitted with a liquid-nitrogen-cooled silicon charge-coupled device detector.

To generate one-dimensional and 2D CL maps, the beam was incrementally scanned, and a spectrum was collected at each position. The electron beam step size, and therefore the pixel size, was 10 nm. The CL spectra and sinogram in FIGS. 4B and 4D, respectively, were smoothed by averaging the central three pixel lines (30 nm) of the 2D map, as well as by averaging over wavelengths in a ±5 nm range. Spectral noise in the CL maps and tomograms was reduced by averaging over wavelengths in a ±5 nm range.

Plane-wave and dipole excitation of the nanocup were modeled using 3D FDTD techniques, with 'FDTD Solutions' by Lumerical Solutions. Electron beam excitation was modeled using a BEM technique. In all cases, the simulated nanocup had the following geometrical parameters: 270 nm diameter gold shell (permittivity from the CRC Handbook of Chemistry and Physics); 200 nm diameter dielectric core (index=1.47), offset in the +z direction by 32.5 nm; 145 nm diameter tip gap; 5.5 nm radius of curvature of the tip; 1 nm mesh size. The extinction cross-section under plane-wave excitation was calculated as the sum of the scattering and absorption cross-sections using a total-field—scattered-field source approach. The PF for a given position and orientation was calculated as the ratio of the power emitted to the far field by a dipole to the power emitted by a dipole in free space. The total PF at a given position was calculated by averaging the contributions from the three orthogonal orientations.

For tomographic reconstruction, filtered back-projection was used to reconstruct 3D functions from 2D projections. A ramp filter multiplied by a Hann window was used both to increase the contrast and to decrease the noise in the reconstructions. Additional details are provided below.

PL spectra were collected from individual nanocups on a PDMS substrate, using a focused continuous-wave argon ion laser operated at 488 nm. The PL spectrum shown in FIG. 8D represents the average of six normalized single-particle spectra. Dark-field scattering spectra were collected before and after laser illumination to guarantee that the nanocups had not been damaged during experimentation.

Simulation, Calculation and Analysis

Nanocup Mode Simulation

Figure 10:
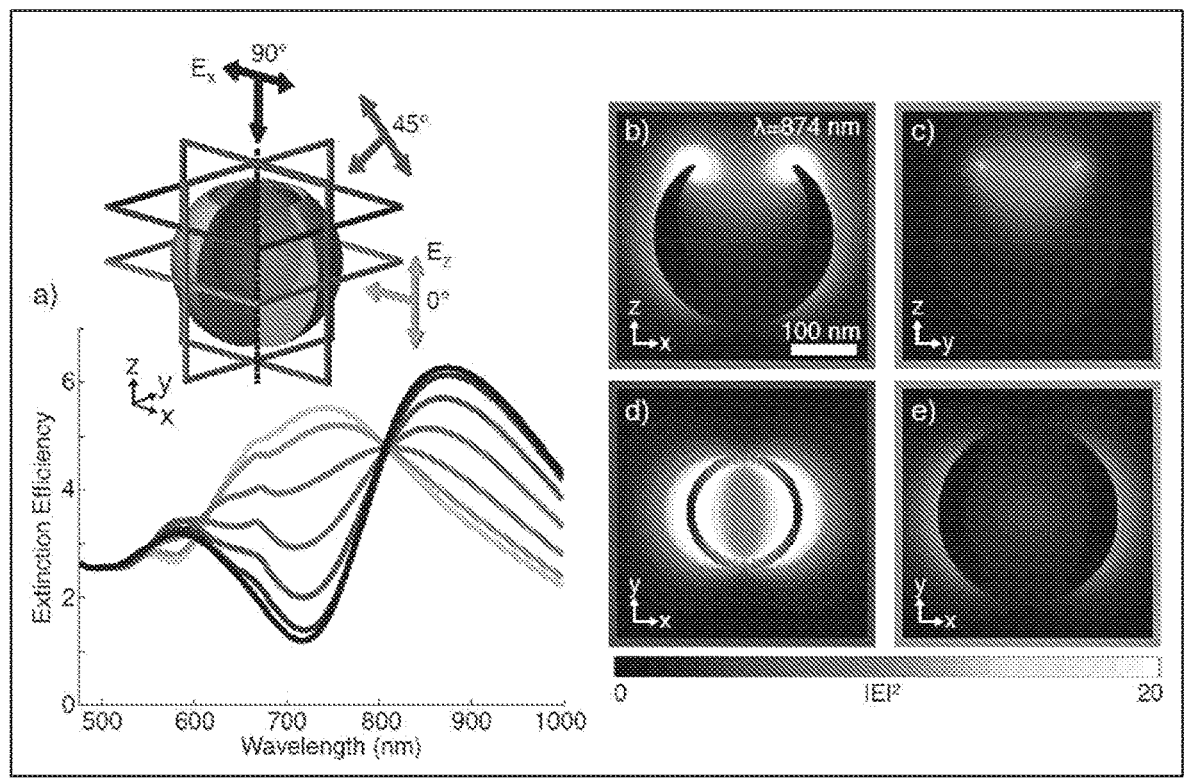
FIG. 10 represents an example of extinction spectra.

The plasmonic modes of the nanocup were determined by exciting the structure with plane waves in FDTD simulations. The extinction efficiency (the ratio of the extinction cross section to the geometrical cross section) was calculated for various angles of incidence, θ, where θ is the angle between the nanocup axis of symmetry and the polarization of the electric field in the (x, z) plane. The extinction spectra for angles between 0° and 90°, in 15° increments, are shown in FIG. 10. A number of different modes can be identified from the extinction spectra. The lowest energy mode at approximately 874 nm, excited most efficiently at 90°, is characterized by strong electric field enhancement in the tip gap of the nanocup. This mode peaks at approximately 850 nm in the CLA experiments, in agreement with the model. The nature of this mode is illustrated in FIG. 10 in the panels labeled (b)-(e), in plots of the calculated intensity of the scattered electric field at 874 nm for a nanocup oriented at 90° at various slices. The slices represent a central cross section in the (x, z) plane in (b), a central cross section in the (y, z) plane orthogonal to the direction of electric field polarization in (c), in the (x, y) plane at the position of the tip gap in (d), and in the (x, y) plane at the center of the nanocup in (e). From the simulated cross sections shown in FIG. 10, it can be seen that this mode (at 874 nm wavelength) is characterized by strong field enhancement primarily in the tip gap of the nanocup, which agrees well with the experimental CLA tomogram.

Another mode, at approximately 740 nm, is efficiently excited at 0°, when the electric field is oriented in the z-direction. This mode is also accessible with a z-oriented dipole or an electron beam propagating along z, and is thus observed in the multi-nanocup tomogram.

Another mode is the highest energy mode, at approximately 580 nm, which is most efficiently excited at 90° and is characterized by an enhanced field near the base of the nanocup. To understand the peaks in the CL spectra at high energies, one should consider not only the radiative decay of plasmonic modes, but also the luminescence from gold and polystyrene. Radiation in gold occurs when an electron in the 'd.' band is excited to an unoccupied state in the 'sp' conduction band. Some fraction of these excited electrons recombine radiatively with the holes in the 'd' band, resulting in emission of a visible photon. This interband transition process may be studied by exciting the gold with light using PL spectroscopy. For smooth gold films, the PL quantum yield is as low as $10^{-10}$, and this source of radiation is therefore often ignored in many CLA experiments. However, it has been shown that nanoparticles of gold exhibit PL quantum yields as high as 0.04, more than eight orders of magnitude higher than gold films.

Figure 11A:
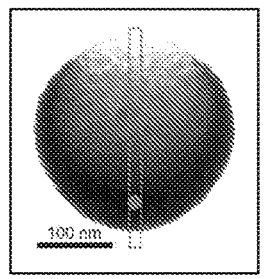
FIG. 11A is an image of an embodiment of a nanocup.
Figure 11B:
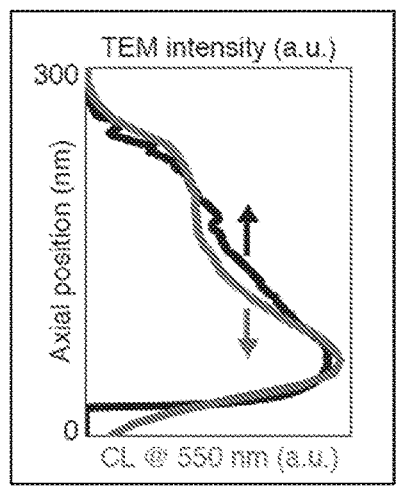
FIG. 11B represents a line scan of transmission electron microscopy intensity along a central axis of the nanocup in FIG. 11A.

To demonstrate that radiation from electron-hole pair recombination in gold contributes to the CL measurement of nanocups, both CL and PL from nanocups are considered. FIG. 11A is a TEM image of a nanocup, where the intensity corresponds to the amount of gold at each location. A line scan of the TEM intensity along the central axis of the nanocup in FIG. 11A is plotted in FIG. 11B, where it can be seen that the gold density peaks in the base of the nanocup as expected for this geometry. Overlaid in FIG. 11B is a line scan of the measured CL intensity along the central axis at a wavelength of 550 nm, where gold is known to fluoresce. By comparing these two curves, it is seen that the CL intensity at 550 nm tracks the gold density. The fact that CL is correlated with the amount of gold the electron interacts with suggests that luminescence from gold contributes significantly to the CL measurement at this wavelength.

Figure 11C:
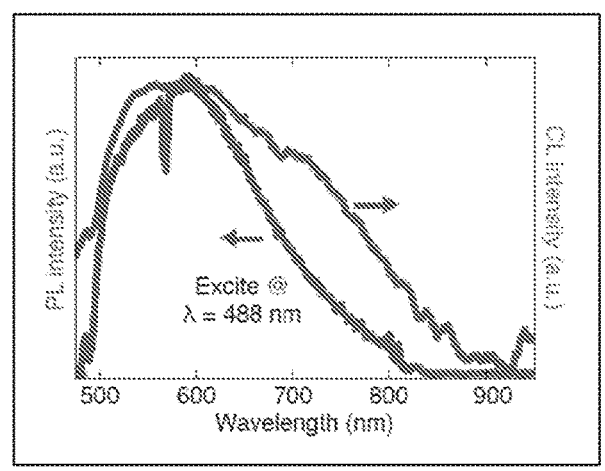
FIG. 11C represents average results for photoluminescence spectra of six nanocups.

To confirm that CL is correlated with the amount of gold that an electron interacts with, the PL was measured for individual nanocups excited at 488 nm with a CW argon ion laser. FIG. 11C provides average results (darker line) for the PL spectra of six single nanocups. The spike at 568 nm is due to the dominant Raman line (—$CH_3$ symmetric stretch, 2886/cm) of the PDMS substrate used in this experiment, which shows up as a dip in the spectrum due to imperfect background subtraction. Overlaid (lighter line) is the CL spectrum at the axial position in the base of the nanocup where the peak gold density is found (as indicated from FIG. 11B, and at the dot in FIG. 11A). This CL spectrum was generated using a multi-nanocup reconstruction technique as described above. Both the PL and the CL spectra peak near 595 nm, and exhibit similar spectral shapes. The increased breadth of the CL spectrum may be due to the broadband nature of the electron beam as an excitation source, as compared to the highly narrowband characteristic of the laser used for PL experiments, or may be due to the different temporal characteristics of the excitation.

The strong spatial agreement illustrated by FIG. 11B, and the spectral agreement illustrated by FIG. 11C, suggest that radiation due to electron-hole pair recombination in gold is responsible for a significant portion of the nanocup CL measured at short wavelengths.

Figure 11D:
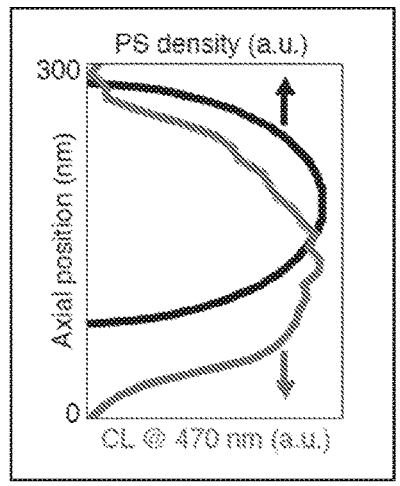
FIG. 11D represents a line scan of the density of polystyrene along the central axis of the nanocup in FIG. 11A.
Figure 11E:
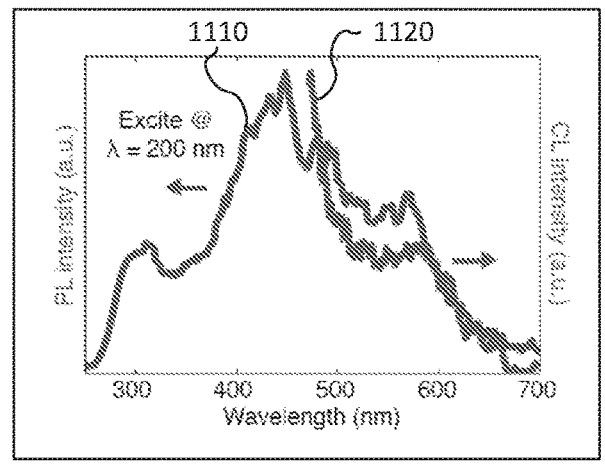
FIG. 11E represents a photoluminescence spectrum, smoothed by averaging over neighboring wavelengths, for the nanocup in FIG. 11A.

Another source of CL measured at the shortest wavelengths probed in this experiment is luminescence from the polystyrene core of the nanocup, as shown in FIGS. 11D and 11E. A line scan of the density of the polystyrene along the central axis of the nanocup is plotted (darker line) in FIG. 11D, calculated based on the nanocup geometry used in FDTD simulations. This is compared to a line scan (lighter line) of the CL intensity along the central axis at a wavelength of 470 nm, at which polystyrene is known to photoluminesce. While some CL measured at this wavelength is likely due to gold luminescence and radiative decay of the high energy plasmonic modes, the shape of the CL spectrum suggests that a portion of the signal is originating from the dielectric core (compare FIG. 11B to FIG. 11D).

To confirm that the 200 nm diameter polystyrene beads used as the core of the nanocups exhibit PL in this spectral regime, PL measurements were taken of polystyrene beads suspended in water using a Cary Eclipse fluorescence spectrophotometer. The excitation was centered at a wavelength of 200 nm and the emission collected after a delay of one microsecond to avoid Raman scattering. The PL spectrum 1110, smoothed by averaging over neighboring wavelengths in a ±5 nm range, is plotted in FIG. 11E, and is seen to peak at 450 nm, in good agreement with previous studies. Also plotted in this figure is the CL spectrum 1120 from the single-nanocup reconstruction, at the axial position at the center of the polystyrene core of the nanocup (as indicated by the PS density curve in FIG. 11D). In comparing these spectra, it is important to keep in mind that the luminescence of polystyrene will be modified by the presence of the gold shell. Although the PL from polystyrene beads is relatively broad, the CL is only clearly observed within the dielectric bead in the 3D tomograms (FIG. 9) at the shortest wavelengths because radiation from the gold shell becomes dominant beyond 500 nm.

Of course, understanding the plasmonic resonances supported by the nanocup at these short wavelengths is also important when interpreting the CL measurements, as radiative decay of these modes will contribute to the overall CL measured. The nature of the high energy nanocup mode is elucidated by plotting the intensity of the scattered electric field at 580 nm, the peak in the extinction efficiency at high energies, when illuminated with a field polarized in the x-direction, as shown in FIG. 4E. It can be seen that the field enhancement is localized to the base of the nanocup, both inside and outside of the metallic shell. This is in contrast to the lowest energy mode at 874 nm, which exhibits the highest field intensity in the tip gap of the nanocup. The high energy mode localized near the metallic base, while also excited directly by the electron beam, most likely enhances the radiation from gold near the base of the nanocup.

The physical localization of this high energy CL is confirmed by examining the CL tilt series. CL line scans of nanocups at angles between 0° and 165°, in 15° increments, were collected, and the normalized intensities at 550 nm used to form the sinogram shown in FIG. 4F. The dashed sine curve overlay denotes the physical position of the center of the base of the nanocup, derived from the nanocup model, which roughly tracks the location of the CL, as expected for the high energy nanocup mode. The downward sloping streak of low CL intensity in the middle of the sinogram corresponds to regions where the electron passes through relatively little gold, and consequently where less gold luminescence is emitted at this wavelength. This sinogram therefore suggests that the high energy CL is comprised of both radiative decay of the high energy nanocup mode as well as radiation from electron-hole pair recombination in gold.

CL maps of nanocups with different orientations help illustrate this point more completely. FIGS. 6A-6D show schematics, SEM images, and 2D CL maps at 550 nm for nanocups at angles of 90°, 120°, and 150°, respectively. The CL maps allow visualization of where the most efficient excitation occurs at this short wavelength. As expected, for each nanocup angle, the CL is highest towards the base of the nanocup and where the gold is thickest. Note that these maps are part of a tilt-series of 7 nanocups used to reconstruct the CL in three dimensions via tomography.

Another way to understand the spatial and spectral dependence of nanocup CL is to compare CL line scans of nanocups at different angles, as shown in FIG. 6D for angles of 90°, 120°, and 150°. Here, the gradient (line darkness) of the different spectra correspond to the different excitation positions along position bar 610. At short wavelengths, the CL peaks consistently near the base of the nanocup (lighter lines) where the high energy modes are excited and where the metallic shell is at its thickest. At longer wavelengths, the peak centered in the 800-850 nm spectral range (darker lines) decreases in magnitude for increasing nanocup angle. This is due to reduced coupling to this mode at 180° (or 0°) when the electron beam is parallel to the nanocup axis of symmetry. However, this mode is excited at most angles, and the slight shift in spectral position is likely due to small differences in tip geometry.

BEM Simulations of CL

The CLA experiments were simulated using a BEM technique. This technique models the fields generated by the swiftly moving electron and is used to simulate the coherent portion of the CL, including radiative decay of electromagnetic eigenmodes and transition radiation. It is important to note, however, that this technique does not reproduce the incoherent portion of the CL, namely material luminescence.

The nanocup-like geometry used in the BEM simulations is the same as that used for the FDTD simulations. Due to geometrical constraints of the code, the nanocups are simulated in free space, ignoring the influence of the substrate, which should be minimal as described in a subsequent section.

Figure 12:
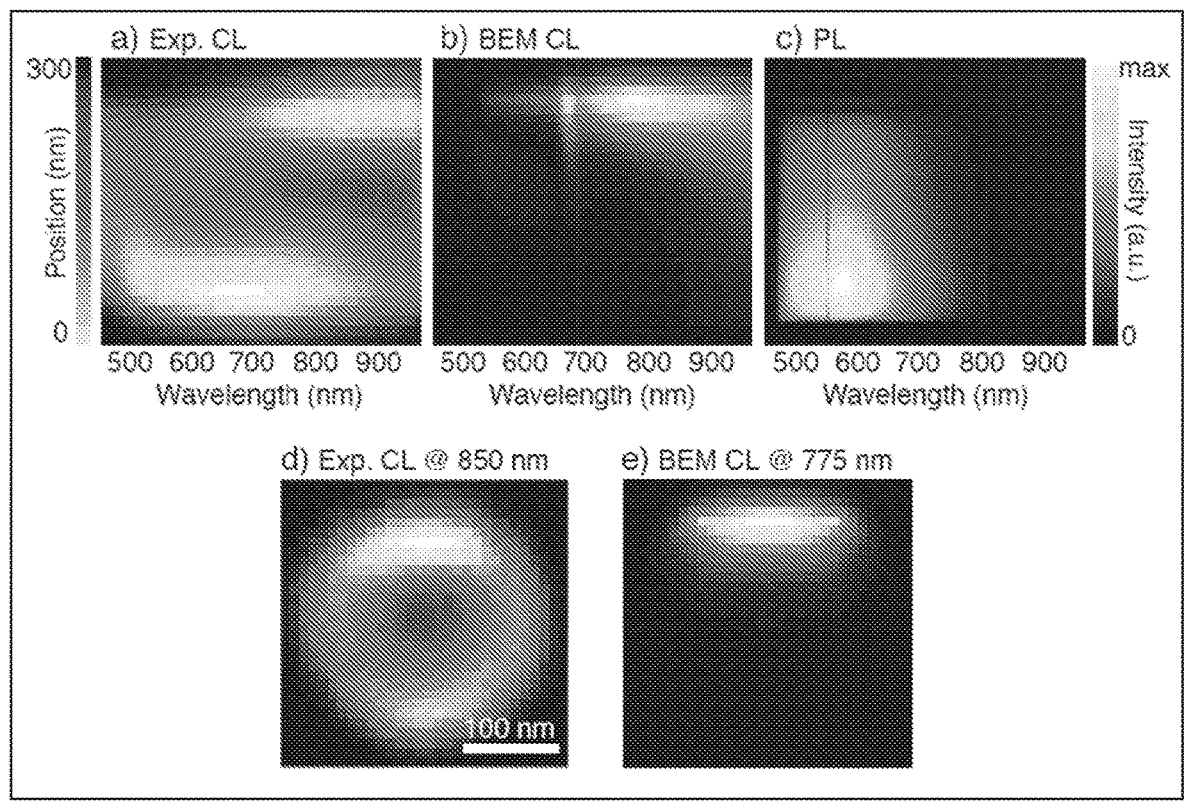
FIG. 12 represents an example of results of boundary element method CL simulations for a nanocup oriented at 90°.

FIG. 12 shows the results of BEM CL simulations for a nanocup oriented at 90°. For reference, FIG. 12 panel (a) is a map of the experimental CL line scan for electron beam positions along the nanocup central axis. FIG. 12 panel (b) represents the same data as calculated via BEM. Note that the bright feature at long wavelengths near the tip of the nanocup is present in both the experiments and the BEM CL simulations. This signal is due to the radiative decay of the plasmonic mode of the nanocup (see, e.g., FIG. 4C and related description), which is efficiently excited by the electron beam. On the other hand, the feature at shorter wavelengths near the base of the nanocup in the CLA experiments is absent in the BEM CL simulations. This discrepancy indicates that the high-energy mode illustrated in FIG. 4E is not efficiently excited by the electron beam. Thus, the short wavelength CL at the base of the nanocup in the experiments must be due primarily to material luminescence, as this type of signal is not accounted for in the BEM simulations.

The material luminescence at the base of the nanocup is best understood by considering the PL of the nanocups stemming from the gold shell, as discussed above. FIG. 12 panel (c) shows a spatial line scan of the PL spectrum weighted by the density of gold as determined by the TEM image, to serve as a qualitative approximation of the strength of the gold luminescence as a function of beam position in the CLA experiment. The gold PL resembles the experimental CL at short wavelengths near the base of the nanocup. Recall that the increased spectral breadth of the CL compared to the PL is most likely due to the broadband nature of the electron beam as an excitation source, as compared to the extremely narrowband character of the laser used for PL experiments.

FIG. 12 panel (d) shows an experimental 2D CL map at a wavelength of 850 nm for a nanocup oriented at 90°. FIG. 12 panel (e) shows the 2D CL map calculated using BEM at 775 nm, the peak wavelength in the simulations. These maps illustrate the excellent agreement between experiment and theory for the plasmonic tip mode. The weak signal in the metallic shell in the experimental map is due to material luminescence, which is not accounted for in the simulations.

Electron-Sample Interaction Simulations

Many factors can influence the physical limits of resolution of the CLA tomography technique. For example, the lateral resolution of CL imaging may be limited by the spot size of the electron beam and the radial extent of the evanescent field associated with the swiftly moving electron. Given an accelerating voltage of 30 kV and a beam spot diameter of approximately 10 nm, a lateral resolution of 30-40 nm has been determined.

The resolution in the third dimension will depend on complex interactions of the electrons with the sample, and is therefore dependent on the particular sample. To estimate the effect of electron-sample interactions on resolution for the nanocups of this disclosure, electron trajectories were simulated using a 3D Monte Carlo analysis. Due to the constraints of the simulation capabilities, a simplified nanocup-like object was analyzed as representative of the nanocup. The nanocup-like object was a 270 nm diameter gold sphere with a 200 nm diameter polystyrene sphere enclosed within it. The center of the polystyrene sphere was displaced by 69 nm with respect to the center of the gold sphere, such that the gold shell has a thickness of 1 nm at its thinnest point, which corresponds to the center of the tip gap in the nanocup. A beam diameter of 1 nm was used in the analysis.

Figure 13:
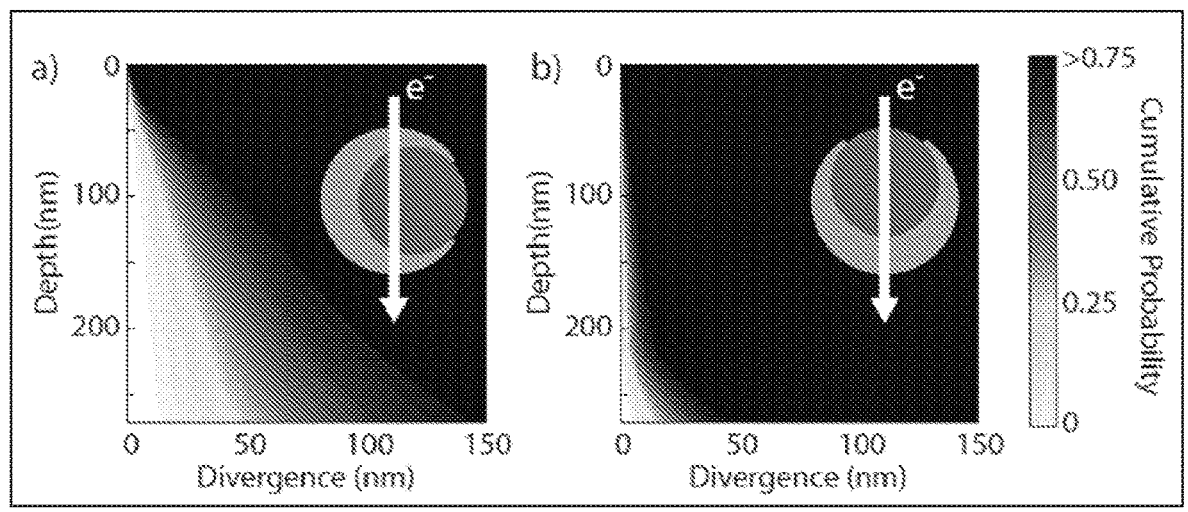
FIG. 13 represents an example of electron-sample interactions.

The divergence of the beam was statistically determined by tracking the trajectories of 10,000 electrons as they passed through the nanocup-like object in a particular orientation. FIG. 13 depicts the electron-sample interactions for two nanocup-like object orientations. As indicated in FIG. 13, for a 30 keV electron beam, fifty percent (50%) of the electrons deviate from their original path after passing through the whole of the nanocup-like object structure in a vertical orientation by less than 25 nm, and in a horizontal orientation by less than 80 nm. Accordingly, beam width averaged over the entire thickness of the nanocup-like object is between 12 and 70 nm. This unavoidable beam divergence influences the effective lateral resolution of a 2D CL image, and thus the resolution of the 3D tomograms. Note, however, that the 2D CL map calculated with BEM in FIG. 12 panel (e), which assumes zero beam divergence, corresponds well to the experimental 2D CL map of FIG. 12 panel (d). Additionally, the CL voxel spectra in FIGS. 8B and 8C correspond well with the LDOS (FIG. 8D) calculated for discrete points using FDTD. Generally, the agreement between experiments and theory indicate that beam divergence is not a significant issue for CLA tomography of the metal-dielectric nanocup. It is worth noting that the divergence of the beam is reduced by an order of magnitude for 300 keV electrons, such as can be obtained in a TEM.

Tomographic Reconstruction by Filtered Back Projection

Tomography is used for creating images of an object based on a series of projections. A brief summary of tomographic reconstruction in two dimensions based on filtered back projection is next described.

Consider a function f (x, y) to be reconstructed. A line 'L' which sits a distance 'p' away from the origin and whose normal forms an angle θ with the x axis can be described by the parametric equation p=x cos θ+y sin θ. The projection of the function f at angle θ is defined as the line integral of function f along 'L', and is known as the Radon transform, as given in equation 1, where the projection vector $g_0$ is composed of line integrals along lines parallel to 'L' at various values of 'p'.

$$g_\theta(p) = \int_{y=-\infty}^{\infty} \int_{x=-\infty}^{\infty} f(x, y)\delta(x\cos\theta + y\sin\theta - p)dx\,dy \qquad (1)$$

The projection vector is converted into the frequency domain to allow filtering by multiplication rather than convolution. The projection vector in the discrete Fourier domain is calculated with a Fourier transform, and is given by equation 2, where N is the number of points in the original projection vector.

$$G_\theta = \sum_{n=0}^{N-1} g_{\theta,n} \exp\left(-\frac{i2\pi k n}{N}\right) \quad k = 0, 1, \ldots, N-1 \qquad (2)$$

This function is then multiplied by a frequency filter, H, resulting in a filtered projection in the frequency domain, $\tilde{G}$=GH, where $\tilde{G}$ indicates a filtered function. The filter is chosen to reduce the contribution of low frequencies while boosting higher frequencies, $$H = \upsilon \left(0.5\left(1 - \cos\left(\pi \frac{\upsilon - \upsilon_{max}}{\upsilon_{max}}\right)\right)\right) \quad 0 \leq \upsilon \leq \upsilon_{max} \quad (3)$$

ultimately yielding a sharper back projection. The simplest version of such a filter is a ramp filter, whose frequency response is given by $|\upsilon|$. To reduce high frequency noise, however, this ramp filter is multiplied by a low pass filter, a window function that tails off at higher frequencies. Here, a Hann window is used, resulting in an overall frequency filter as given in equation 3, where $\upsilon_{max}$ is chosen to be the sampling frequency, which is determined by the resolution of the original projections.

The filtered projection is returned back to the spatial domain by taking the real part of the inverse discrete Fourier transform of $\tilde{G}$, as given in equation 4.

$$\tilde{g}_\theta(p) = \mathrm{Re}\left(\frac{1}{N}\sum_{k=0}^{N-1} \tilde{G}_{\theta,k} \exp\left(\frac{i2\pi k n}{N}\right)\right) n = 0, 1, \ldots, N-1 \quad (4)$$

Back projection is used to convert this filtered projection vector into a 2D function. At a single angle, $\theta_m$, the back projection is calculated as in equation 5.

$$f_{B,\theta_m}(x,y) = \tilde{g}_{\theta_m}(x\cos\theta_m + y\sin\theta_m) \quad (5)$$

From equation 5, and given that the value of 'p' is the same for all (x, y) that lie on line it can be understood that the filtered projection makes the same contribution to the back projection at all points (x, y) that lie on 'L'. In this way, the filtered projection is smeared back, or back projected, over the reconstructed image plane.

The accuracy of the reconstruction is dramatically improved through the use of projections at multiple angles. The reconstructed function is calculated as the sum of the back projections at each angle, as shown in equation 6, where M is the number of projections, or angles, used in the reconstruction.

$$f_{B,total}(x, y) = \sum_{m=0}^{M-1} f_{B,\theta_m}(x, y) \Delta\theta \quad (6)$$

For a complete reconstruction, angles between 0 and $\pi$ are used, and therefore $\Delta\theta = \pi/M$. A visual illustration of this back projection technique is given in a later portion of this disclosure. The 2D filtered back projection technique can be also used to reconstruct a 3D function f (x, y, z) by reconstructing the function f (x, y), as described above, for each value of z.

TEM Tilt Series and Reconstruction

Figure 14:
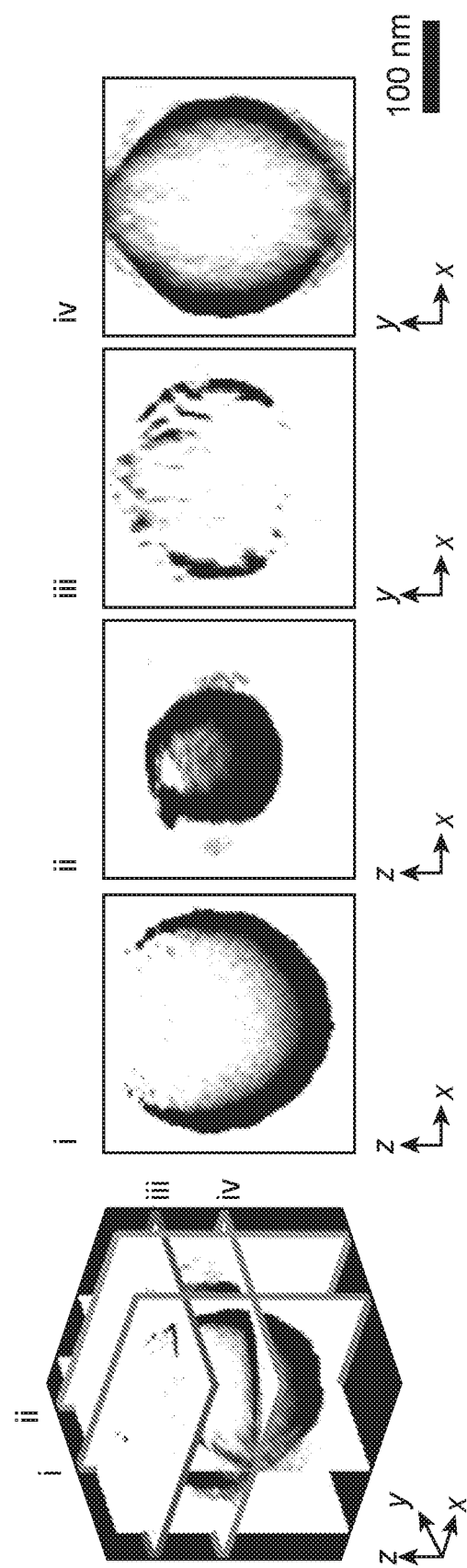
FIG. 14 represents an example of a 2D reconstruction of a nanocup based on a tilt-series.

To confirm the 3D structure of the nanocup and justify the assumption of rotational symmetry used in creating the CLA tomograms, bright-field TEM images are obtained of a nanocup at many different angles. These images form two orthogonal tilt-series, each spanning 110° degrees and containing 23 images. This double tilt-series of TEM images can also be used to reconstruct the structure of the nanocup. The 3D reconstruction of the nanocup based on the tilt-series is shown in FIG. 14. Note that panels (i) through (iv) of this reconstruction correspond remarkably well to panels (i) through (iv) of FIG. 7A, which represent TEM reconstruction based on a single TEM image and assuming rotational symmetry. The effect of a missing wedge of information, however, is readily apparent in the tilt-series reconstruction shown here, by the stretching of the circular cross section in panel (iv), which is a reconstruction artefact caused by the fact that projections are available up to a limited angle (in this case 55°).

Reconstructed Nanocup Geometry

To define the nanocup geometry for modeling purposes, the geometry of the TEM reconstruction was considered. Based on the reconstruction, the nanocup was modeled with a 200 nm diameter dielectric core and a 270 nm diameter gold shell displaced by 32.5 nm. The tip gap is selected to be 145 nm, resulting in a tip with a radius of curvature of 5.5 nm. A side-by-side comparison of the central slice of the reconstruction to the central slice of the model is given in FIG. 15A. Visual inspection suggests that the simulated geometry (model, to the right of the dotted line) is quite similar to the TEM reconstruction (experiment, to the left of the dotted line), aside from the detailed tip geometry.

Figures 15A, 15B, 15C:
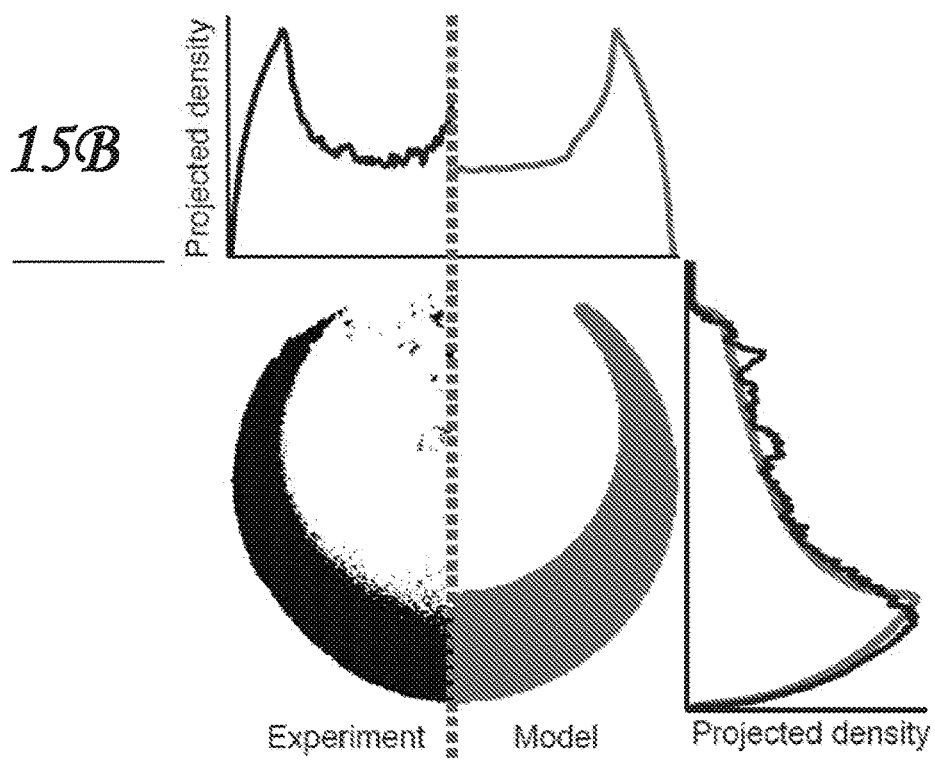
FIGS. 15A, 15B and 15C represent an example of comparison of a CL reconstruction to a model.

To quantitatively compare the two geometries, the densities of the experimental and modeled geometries is also graphed along two orthogonal axes. FIG. 15B depicts the projection in the vertical direction, and FIG. 15C depicts the projection in the horizontal direction. These projected densities illustrate the excellent agreement between the model geometry and the experimental TEM reconstruction.

Effect of Substrate on Nanocup Tilt Series

To construct a tilt-series of nanocups for tomographic reconstruction, distinct nanocups with different orientations relative to the substrate are used. This is due to the inability to tilt the sample in the CL SEM of this example demonstration. An important assumption of this multi-particle tomography technique is that the properties under study are not significantly affected by the substrate. This assumption is justified by considering two important dipole locations, as shown in FIGS. 16 and 17.

Figure 16:
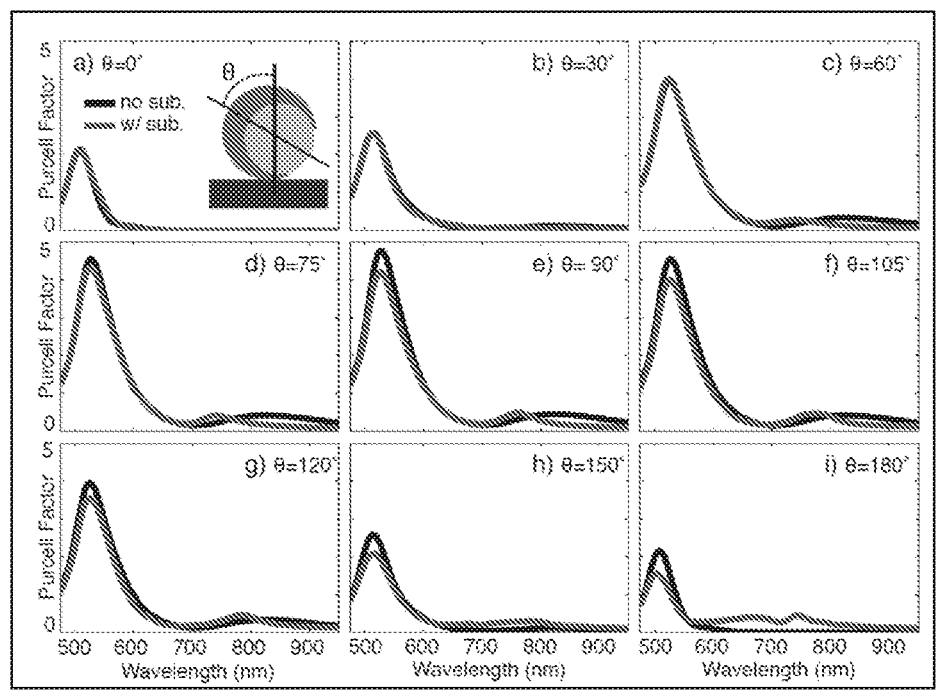
FIG. 16 represents examples of radiative rate enhancement.

The first dipole is located in the metal base of the nanocup, 55 nm from the outer edge, as depicted in the schematic inset in panel (a) of FIG. 16. This dipole location is chosen because of the importance of metal luminescence in the CL. The second dipole is located in the dielectric core of the nanocup, 72.5 nm from the outer edge along the nanocup axis of symmetry, and oriented perpendicular to the substrate (refractive index=3.7), as depicted in the schematic inset in panel (a) of FIG. 17. This dipole location is chosen for its ability to excite both the low energy gap mode at the tip of the nanocup, as well as higher energy modes. The angle between the nanocup axis of symmetry and the substrate normal is defined as $\theta$. Note that in the absence of particle-substrate interactions, angles of $\theta$ and $180°-\theta$ would give the same response.

Figure 17:
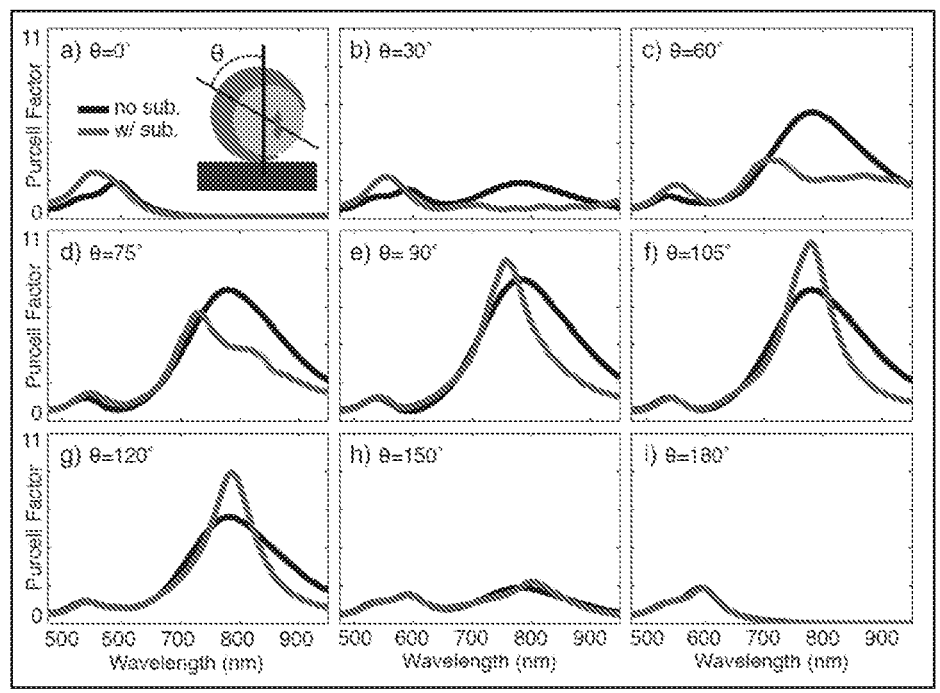
FIG. 17 represents examples of radiative rate enhancement.

FIG. 16, panels (a)-(i) and FIG. 17, panels (a)-(i) plot PF, or radiative rate enhancement, spectra for angles of 0°, 30°, 60°, 75°, 90°, 105°, 120°, 150°, and 180°, respectively in the lighter curves. The darker curves represent the PF when no substrate is present. FIG. 16 demonstrates that the substrate has a negligible effect on the LDOS within the base of the metallic shell of the nanocup. In FIG. 17, it can be seen that there is some substrate effect, but it is minimal, especially for angles of 75° and above, the effect of the substrate is minimal. For these reasons, the multi-nanocup tomographic reconstruction may be performed in some embodiments using a tilt-series composed of nanocups at angles of approximately 75° and above.

CL Reconstruction

FIG. 18 elucidates the reconstruction of the CL by the technique of filtered back projection. The technique is explained for ease of understanding with respect to a single CL image, but the technique is general and is used for the reconstruction based on the full tilt-series as well. FIG. 18, panel (a) shows a CL map at 850 nm for a nanocup oriented at 90°, with its axis of rotational symmetry perpendicular to the incident electron beam. Assuming the nanocup is rotationally symmetric and ignoring any substrate effects, this CL map is used as a virtual tilt-series spanning the full 360° of rotation.

As discussed above, the 3D reconstruction is accomplished by carrying out a 2D reconstruction in the (x, y) plane at each value of z. For the example of FIG. 18, an intermediate value of z is chosen, as highlighted by the box in panel (a). This data is a CL line scan through the nanocup, perpendicular to its axis of symmetry, as shown by the darker curve in panel (b) of FIG. 18, where data points beyond the boundaries of the scan have been set to zero. The lighter curve in panel (b) is the CL intensity after being filtered in the frequency domain by a ramp filter multiplied by a Hann window, as given in Equation 3. To illustrate the back projection technique, reconstructions using an increasing number of angles are given in panels (c) through (f) of FIG. 18. When only a single angle, 0°, is used for the reconstruction (panel (c)), it can be seen that the filtered function is simply smeared across the reconstructed image plane in the vertical direction. When two angles, 0° and 90°, are used (panel (d)), the vertical and horizontal back projections sum to give a square-like pattern. With four angles 0°, 45°, 90° and 135° (panel (e)), the donut-like form begins to take shape. Panel (f) shows a reconstruction using 360 angles, or a projection at every degree. From these figures it is clear that the accuracy of the reconstruction is dramatically improved through the use of projections at multiple angles. However, it is also important to note that even with only four angles, the general shape of the reconstructed function is apparent. This indicates that the tomogram based on tilt-series data using multiple angles (e.g., four or more) will capture the essence of the 3D CL. In one or more embodiments, fourteen angles are used.

CLA Tilt Series Reconstruction and Re-Projection

As discussed above, while the rotational symmetry of the nanocup allows for a simple reconstruction of the CL from a single CL map, this symmetry is not a requirement of the CLA tomography technique.

The CL may be reconstructed using CL maps of nanocups at different orientations. For this tilt-series, consider nanocups with angles between 75° and 165°, in 15° increments, ignoring angles between 0° and 60° for the reasons stated above. Due to the reflection symmetry of the nanocup, nanocups at angles between 75° and 165° are equivalent to those at angles between 195° to 285°, and thus the tilt series is composed of 14 different angles. In order to reduce the effect of the angular dependence of the excitation of the various modes, the intensities of the 2D maps are normalize in the tilt-series at each wavelength prior to reconstruction. Thus, although the angular dependence strictly breaks the projection requirement, the effect is reduced, and the resulting qualitative reconstruction still provides useful information about the existence and 3D distribution of excitable modes in the structure. The rotational symmetry is imposed during reconstruction to enhance the tomograms.

Figure 19:
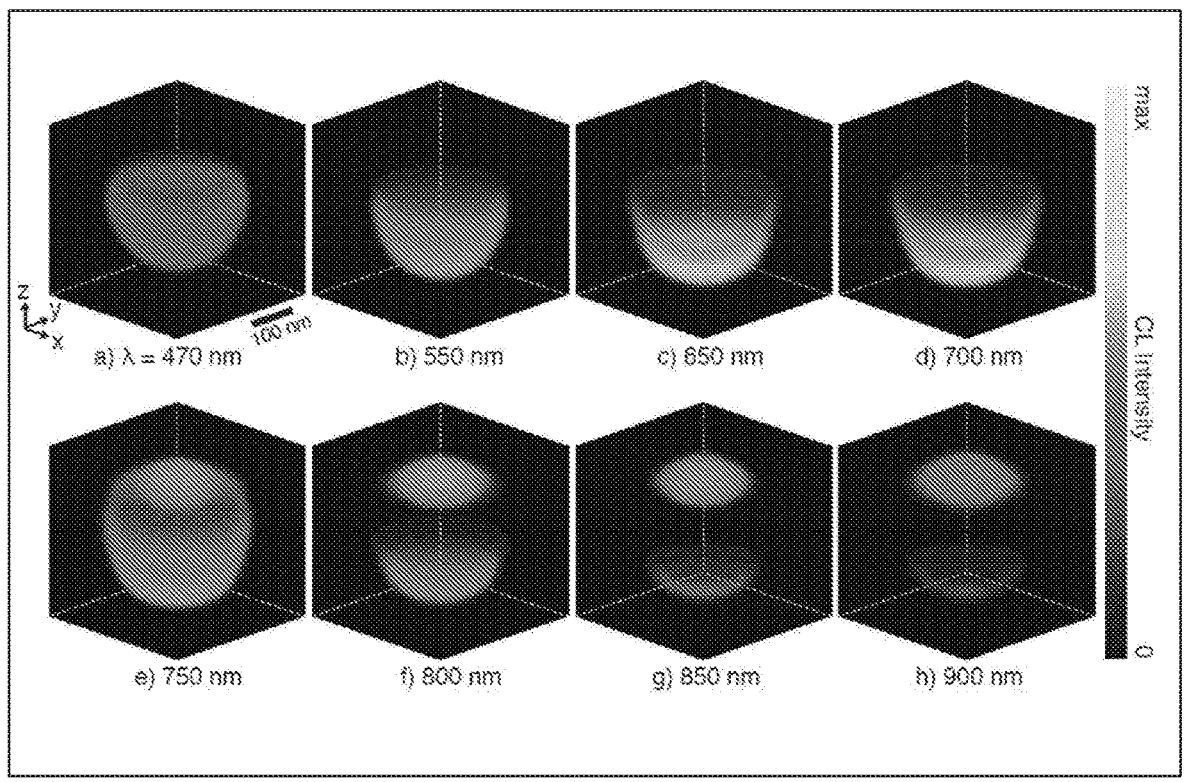
FIG. 19 represents examples of 2D CL tomograms.

FIG. 19 shows eight 3D CL tomograms at wavelengths between 470 nm and 950 nm, where the intensity of the reconstructed function corresponds to both the gradation scale and the transparency of the figure. These eight CL tomograms agree well with CL tomograms generated from the single nanocup virtual tilt series. For shorter wavelengths the CL is concentrated primarily in the metallic shell of the nanocup, as expected for radiation from the gold. At longer wavelengths, efficient excitation of the gap mode can be seen clearly towards the top of the tomograms, near the tip of the nanocup, as predicted by theory.

To confirm the quality of this multi-nanocup reconstruction, the reconstructed volumes are re-projected at the same angles as were obtained in the experiment. These re-projections, along with the original 2D CL maps of nanocups at various angles, are provided in FIG. 7D. The excellent agreement between the original maps and the re-projections across the range of wavelengths and angles is indicative of the high fidelity of multi-nanocup reconstruction. This comparison is also useful in demonstrating the validity of generating a tomogram from many different nearly identical nanocups (or other object). Recall that the tomograms, and thus the re-projections, are based on 7 different nanocups at 14 different angles. The strong agreement between these re-projections and the 2D CL maps of individual nanocups is an indication of the similarity between the nanocups as well as the validity of the assumptions made.

Purcell Factor Calculations

A comparison of the single- and multi-nanocup reconstructions to PF calculations was provided in FIGS. 8B-8D. A more detailed analysis is provided in FIG. 20. Reconstructed CL spectra at voxels along the central axis of the nanocup for the single- and multi-nanocup reconstructions are shown in panels (b) and (c) of FIG. 20. The spectral maps show good agreement for the plasmonic tip mode at wavelengths around 850 nm, as well as for the material luminescence in the base of the nanocup at shorter wavelengths. However, in the dielectric core of the nanocup, the multi-nanocup reconstruction reveals a peak at around 650 nm not present in the single-nanocup reconstruction.

To identify this feature, calculation is performed of the PF within the nanocup. The average PF is shown in panel (d) of FIG. 20. By comparing the PF for x- or y-oriented dipoles in panel (e) with the PF for a z-oriented dipole in panel (f), it is seen that the peak in the center of the dielectric core in the multi-nanocup reconstruction is due to a mode that is not efficiently excited at 90°, and therefore does not show up in the single-nanocup reconstruction, which ignores modes that specify a z-oriented electron beam for efficient excitation. Recall that this mode is also excited by a plane wave, but when the electric field is oriented in the z direction.

Figure 21:
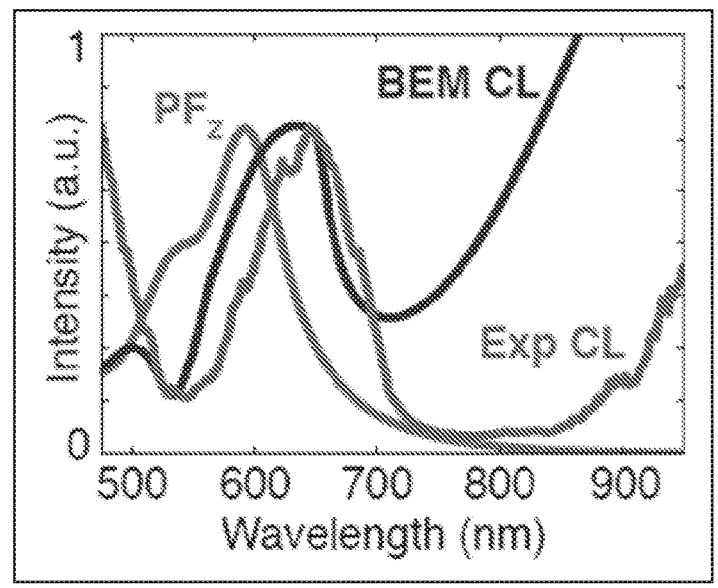
FIG. 21 represents examples of spectra from a multi-nanocup reconstruction.

Additional insight into this feature is provided by BEM CL simulations of a nanocup oriented at 0° (with the nanocup axis of symmetry parallel to the electron beam). FIG. 21 shows a spectrum of the BEM CL intensity for an electron beam at the center of the nanocup, along with the experimental CL intensity at the center of the dielectric core from the multi-nanocup reconstruction. For comparison, FIG. 21 also includes the z-component of the PF at the same position. Note that the shift of the simulated spectra with respect to the experimental spectrum is likely due to the substrate, which is not considered in the simulations. The agreement between these three spectra confirms that the peak at the center of the core of the nanocup is, in fact, a mode that specifies a z-oriented source for efficient excitation. This comparison also demonstrates the ability of the multi-nanocup reconstruction to probe all modes of the system.

As used herein, the term "visible range" refers to a range of wavelengths from about 400 nm to about 700 nm.

As used herein, the term "infrared range" refers to a range of wavelengths from about 700 nm to about 2 mm. The infrared range includes the "near-infrared range," which refers to a range of wavelengths from about 700 nm to about 5 µm, the "middle infrared range," which refers to a range of wavelengths from about 5 µm to about 30 µm, and the "far infrared range," which refers to a range of wavelengths from about 30 µm to about 2 mm.

As used herein, the singular terms "a," "an," and "the" include plural referents unless the context clearly dictates otherwise. Thus, for example, reference to an object can include multiple objects unless the context clearly dictates otherwise.

As used herein, the term "ultraviolet range" refers to a range of wavelengths from about 5 nm to about 400 nm.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable characteristics that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, the terms "approximately," "substantially" and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, technique, operation or operations, to the objective, spirit and scope of the disclosure. All such modifications are intended to be within the scope of the claims appended hereto. In particular, while certain techniques may have been described with reference to particular operations performed in a particular order, it will be understood that these operations may be combined, sub-divided, or re-ordered to form an equivalent technique without departing from the teachings of the disclosure. Accordingly, unless specifically indicated herein, the order and grouping of the operations is not a limitation of the disclosure.

What is claimed is:

1. A cathodoluminescence (CL) spectroscopic tomography device, comprising:
   a sample stage configured to support a sample;
   an electron beam source configured to scan an electron beam over the sample to yield light emission by the sample;
   a light detector;
   a reflective element configured to direct the light emission by the sample to the light detector; and
   a controller coupled to the sample stage, the electron beam source, and the light detector to control operation of the sample stage, the electron beam source, and the light detector, wherein the controller is configured to derive a plurality of two-dimensional (2D) CL maps of the sample from the light emission, the 2D CL maps oriented at different angles relative to an axis through the sample, the controller is configured to derive the 2D CL maps by filtering in a frequency domain, the filtering includes a ramp filter and a low pass filter, and the controller is configured to derive a three-dimensional (3D) CL tomogram of the sample from the plurality of 2D CL maps using filtered back projection.

2. The device of claim 1, wherein the scan of the electron beam over the sample is a line scan, and wherein the controller is configured to derive the 2D CL maps of the sample from the light emission yielded during the line scan.

3. The device of claim 1, wherein the sample is symmetric about the axis.

4. The device of claim 1, wherein a number of the angles is four or more.

5. A method, comprising:
   controlling a detector to measure intensity of emissions from an object resulting from an electron beam scanned across the object;
   receiving from the detector information related to the measured intensity;
   deriving from the received information a plurality of two-dimensional (2D) cathodoluminescence (CL) maps; and
   deriving from the 2D CL maps a three-dimensional (3D) CL map,
   wherein deriving the 2D CL maps comprises using line scan information of a line lying along a plane of the object to derive a 2D CL map of the object over an area of the object at the plane, wherein deriving the 2D CL maps includes filtering in a frequency domain, and the filtering includes a ramp filter and a low pass filter, wherein deriving the 3D CL map comprises using filtered back projection.

6. The method of claim 5, wherein the information related to the measured intensity is information related to intensity measured during line scans of the object.

7. The method of claim 5, further comprising controlling an electron beam source to scan the electron beam over the object.

8. The device of claim 1, wherein the controller is configured to derive the 3D CL tomogram of the sample by summing the 2D CL maps oriented at the different angles.

9. The method of claim 5, wherein deriving the 3D CL map includes summing the 2D CL maps.

* * * * *